United States Patent
Tan et al.

(10) Patent No.: US 11,344,873 B2
(45) Date of Patent: May 31, 2022

(54) MULTI-LAYERED METAL-CARBON MATERIALS-BASED NANOARCHITECTURES

(71) Applicant: Nanyang Technological University, Singapore (SG)

(72) Inventors: Thatt Yang Timothy Tan, Singapore (SG); Zhiping Zeng, Singapore (SG)

(73) Assignee: Nanyang Technological University, Singapore (SG)

( * ) Notice: Subject to any disclaimer, the term of this patent is extended or adjusted under 35 U.S.C. 154(b) by 402 days.

(21) Appl. No.: 16/464,241

(22) PCT Filed: Nov. 29, 2017

(86) PCT No.: PCT/SG2017/050588
§ 371 (c)(1),
(2) Date: May 24, 2019

(87) PCT Pub. No.: WO2018/101887
PCT Pub. Date: Jun. 7, 2018

(65) Prior Publication Data
US 2019/0388883 A1   Dec. 26, 2019

(30) Foreign Application Priority Data

Nov. 29, 2016   (SG) ........................... 10201610003S

(51) Int. Cl.
*B01J 21/18*      (2006.01)
*B01J 23/42*      (2006.01)
(Continued)

(52) U.S. Cl.
CPC .......... *B01J 35/0006* (2013.01); *B01J 21/18* (2013.01); *B01J 23/42* (2013.01); *B01J 23/50* (2013.01);
(Continued)

(58) Field of Classification Search
CPC ... B01J 21/18; B01J 23/42; B01J 23/50; B01J 23/52; B01J 35/0006; B01J 35/0013;
(Continued)

(56) References Cited

U.S. PATENT DOCUMENTS

| | | | |
|---|---|---|---|
| 9,981,247 B2 * | 5/2018 | Chopra | C01B 32/198 |
| 2008/0230782 A1* | 9/2008 | Antoniadis | H01L 31/075 257/53 |
| 2018/0050324 A1* | 2/2018 | Qin | B01J 23/50 |

OTHER PUBLICATIONS

Chang et al. "Electrochemical Impedance Spectroscopy," Annual Review of Analytical Chemistry, Jul. 19, 2010, vol. 3, pp. 207-229, <https://doi.org/10.1146/annurev.anchem.012809.102211>.
(Continued)

*Primary Examiner* — Cam N. Nguyen
(74) *Attorney, Agent, or Firm* — Patterson + Sheridan, LLP

(57) ABSTRACT

Disclosed herein is a multi-layered composite thin film material formed from graphene quantum dots (GQDs) and metal nanocrystals in a layer-by-layer design, wherein the metal nanocrystals can be selected from the group consisting of Ru, Rh, Os, Ir, Pd, Au, Ag and Pt. In a preferred embodiment, the multi-layered composite thin film material is prepared via a facile, green, and easily accessible layer-by-layer (LbL) self-assembly strategy. In this strategy, positively charged GOQDs and negatively charged metal nanocrystals are alternately and uniformly integrated with each other in a "face-to-face" stacked fashion under substantial electrostatic attractive interaction, and then the obtained GOQDs/metal composite thin film is calcined into GQDs/metal composite thin film. The composite thin film material disclosed herein may be used to catalyse a wide range or reactions, including selective reduction of aromatic nitro compounds in water and electrocatalytic oxidation of methanol at ambient conditions.

19 Claims, 26 Drawing Sheets

Figure 1:
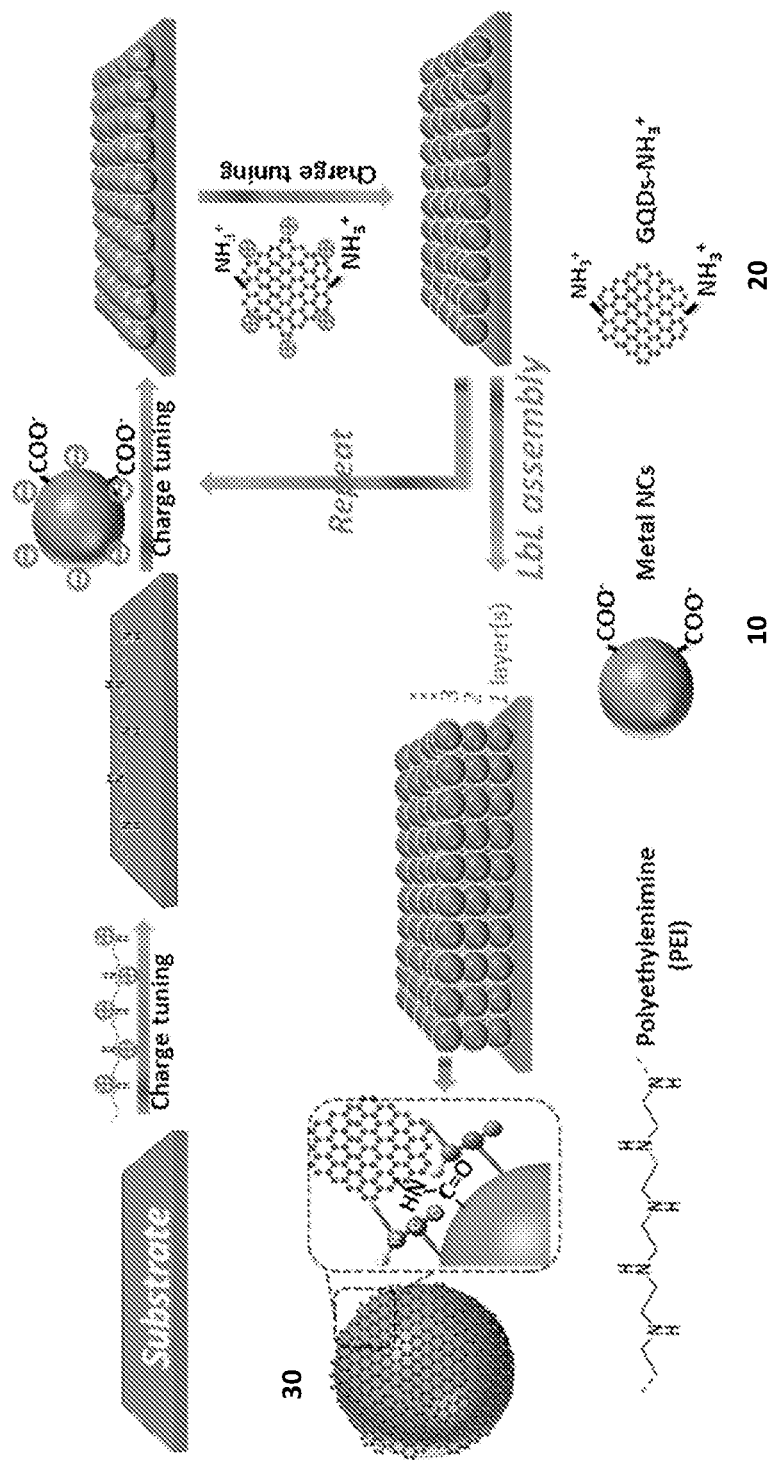

(51) Int. Cl.

| | |
|---|---|
| *B01J 23/50* | (2006.01) |
| *B01J 23/52* | (2006.01) |
| *B01J 35/00* | (2006.01) |
| *B01J 37/02* | (2006.01) |
| *B01J 37/08* | (2006.01) |
| *C25B 1/00* | (2021.01) |
| *C25B 1/04* | (2021.01) |
| *C25B 1/55* | (2021.01) |
| *C25B 11/051* | (2021.01) |
| *C25B 11/091* | (2021.01) |
| *H01M 4/86* | (2006.01) |
| *H01M 4/90* | (2006.01) |
| *H01M 4/92* | (2006.01) |
| *H01M 4/96* | (2006.01) |
| *H01M 8/1011* | (2016.01) |
| *C07C 209/36* | (2006.01) |
| *G01J 1/42* | (2006.01) |

(52) U.S. Cl.
CPC ............ *B01J 23/52* (2013.01); *B01J 35/006* (2013.01); *B01J 35/0013* (2013.01); *B01J 37/0228* (2013.01); *B01J 37/0236* (2013.01); *B01J 37/08* (2013.01); *C07C 209/36* (2013.01); *C25B 1/00* (2013.01); *C25B 1/04* (2013.01); *C25B 1/55* (2021.01); *C25B 11/051* (2021.01); *C25B 11/091* (2021.01); *G01J 1/42* (2013.01); *H01M 4/8657* (2013.01); *H01M 4/9041* (2013.01); *H01M 4/925* (2013.01); *H01M 4/96* (2013.01); *H01M 8/1011* (2013.01)

(58) Field of Classification Search
CPC .. B01J 35/006; B01J 37/0228; B01J 37/0236; B01J 37/08; C25B 1/00; C25B 1/04; C25B 1/55; C25B 11/051; C25B 11/091; H01M 4/8657; H01M 4/9041; H01M 4/925; H01M 4/96; H01M 8/1011; C07C 209/36; G01J 1/42
See application file for complete search history.

(56) References Cited

OTHER PUBLICATIONS

Choi et al. "Graphene Multilayer Supported Gold Nanoparticles for Efficient Electrocatalysts Toward Methanol Oxidation," Advanced Energy Materials, Jul. 26, 2012, vol. 2, No. 12, pp. 1510-1518, DOI: 10.1002/aenm.201200214.

Choi et al. "Hybrid Gold Nanoparticle-Reduced Graphene Oxide Nanosheets as Active Catalysts for Highly Efficient Reduction of Nitroarenes," J. Mater. Chem., 2011, vol. 21, p. 15431-15436, DOI: 10.1039/C1JM12477C.

Dotzauer et al., "Catalytic Membranes Prepared Using Layer-by-layer Adsorption of Polyelectrolyte/Metal Nanoparticle Films in Porous Supports," Nano Letters, 2006, vol. 6, No. 10, pp. 2268-2272, DOI: 10.1021/nl061700q.

He et al. "Understanding TiO2 Size-Dependent Electron Transport Properties of a Graphene-TiO2 Photoanode in Dye-Sensitized Solar Cells Using Conducting Atomic Force Microscopy," Advanced Materials, 2013, vol. 25, No. 47, pp. 6900-6904, https://doi.org/10.1002/adma.201303327.

Hong et al. "Graphene Multilayers as Gates for Multi-Week Sequential Release of Proteins from Surfaces," ACS Nano 2012, vol. 6, No. 1, pp. 81-88, https://doi.org/10.1021/nn202607r.

Jin et al. "Tuning the Photoluminescence of Graphene Quantum Dots through the Charge Transfer Effect of Functional Groups," ACS Nano, 2013, vol. 7, No. 2, pp. 1239-1245, https://doi.org/10.1021/nn304675g.

Lee et al. "Electrocatalytic Properties of Pt Nanowires Supported on Pt and W Gauzes," ACS Nano, 2008, vol. 2, No. 10, pp. 2167-2173, https://doi.org/10.1021/nn800458p.

Li et al. "Processable aqueous dispersions of graphene nanosheets," Nature Nanotechnology,2008, vol. 3, pp. 101-105, https://doi.org/10.1038/nnano.2007.451.

Lou et al. "General Self-Assembly Route toward Sparsely Studded Noble-Metal Nanocrystals inside Graphene Hollow Sphere Network for Ultrastable Electrocatalyst Utilization," ACS Applied Materials & Interfaces, Aug. 25, 2015, vol. 7, No. 36, p. 20061-20067, DOI: 10.1021/acsami.5b05116.

Lu et al. "Transforming C60 molecules into graphene quantum dots," Nature Nanotechnology, 2011, vol. 6, pp. 247-252, https://doi.org/10.1038/nnano.2011.30.

Pei et al. "Graphene oxide quantum dots@silver core-shell nanocrystals as turn-on fluorescent nanoprobe for ultrasensitive detection of prostate specific antigen," Biosens Bioelectron, Dec. 15, 2015, vol. 74, pp. 909-914, DOI: 10.1016/j.bios.2015.07.056.

Ran et al. "Ag Nanoparticle-decorated graphenequantum dots for label-free, rapid and sensitive detection of Ag+ and biothiols," Chemical Communications, 2013, vol. 49, pp. 1079-1081, DOI: 10.1039/C2CC38403E.

Wu et al. "Selective oxidation of veratryl alcohol with composites of Au nanoparticles and graphene quantum dots as catalysts," Chemical Communications, 2015, vol. 51, pp. 6318-6321, DOI: 10.1039/c5cc00061k.

Xiao et al. "Bridging the Gap: Electron Relay and Plasmonic Sensitization of Metal Nanocrystals for Metal Clusters," Journal of the American Chemical Society, 2015, vol. 137, No. 33, pp. 10735-10744, https://doi.org/10.1021/jacs.5b06323.

Xu et al. "A Novel Sensor for Sensitive and Selective Detection of Iodide Using Turn-on Fluorescence Graphene Quantum Dots/Ag Nanocomposite," Analytical Sciences, Aug. 2015, vol. 31, pp. 787-791, DOI: 10.2116/analsci.31.787.

Yan et al. "Electrocatalytic Performance of Gold Nanoparticles Supported on Activated Carbon for Methanol Oxidation in Alkaline Solution," The Journal of Physical Chemistry C, 2011, vol. 115, No. 14, pp. 6986-6993, https://doi.org/10.1021/jp1086834.

Yan et al. "Single-Atom Pd1/Graphene Catalyst Achieved by Atomic Layer Deposition: Remarkable Performance in Selective Hydrogenation of 1,3-Butadiene," Journal of the American Chemical Society, 2015, vol. 137, No. 33, pp. 10484-10487, https://doi.org/10.1021/jacs.5b06485.

Yang et al. "Core?Shell Ag?Au Nanoparticles from Replacement Reaction in Organic Medium," The Journal of Physical Chemistry B, 2005, vol. 109, No. 41, pp. 19208-19212, https://doi.org/10.1021/jp052242x.

Yin et al. "Facile Synthesis of Surfactant-Free Au Cluster/Graphene Hybrids for High-Performance Oxygen Reduction Reaction," ACS Nano, 2012, vol. 6, No. 9, pp. 8288-8297, https://doi.org/10.1021/nn302984x.

Yuan et al. "Direct Modulation of Localized Surface Plasmon Coupling of Au Nanoparticles on Solid Substrates via Weak Polyelectrolyte-Mediated Layer-by-Layer Self Assembly," Langmuir, 2009, vol. 25, No. 13, pp. 7578-7585, https://doi.org/10.1021/la901443x.

Zeng et al. "Layer-by-layer assembly of nitrogen-doped graphene quantum dots monolayer decorated one-dimensional semiconductor nanoarchitectures for solar-driven water splitting," Journal of Materials Chemistry A, Sep. 21, 2016, vol. 4, No. 42, pp. 16383-16393, DOI: 10.1039/c6ta05469b.

Zhu et al. "Layer-by-Layer Self-Assembly for Constructing a Graphene/Platinum Nanoparticle Three-Dimensional Hybrid Nanostructure Using Ionic Liquid as a Linker," Langmuir, Jan. 14, 2010, vol. 26, No. 10, pp. 7614-7618, DOI: 10.1021/la904201j.

Adhikari, Bimalendu, et al.—"Graphene Oxide-Based Hydrogels to Make Metal Nanoparticle-Containing Reduced Graphene Oxide-Based Functional Hybrid Hydrogels," ACS Applied Materials & Interfaces, 2012, 4, pp. 5472-5482.

Cheng, Huhu, et al.—"Graphene-Quantum-Dot Assembled Nanotubes: A New Platform for Efficient Raman Enhancement," ACS Nano, 2012, vol. 6, No. 3, pp. 2237-2244.

(56) References Cited

OTHER PUBLICATIONS

Dotzauer, David M., et al.—"Catalytic Membranes Prepared Using Layer-by-Layer Adsorption of Polyelectrolyte/Metal Nanoparticle Films in Porous Supports," Nano Letters, 2006, vol. 6, No. 10, pp. 2268-2272.
Gui, Jinghan, et al.—"Practical olefin hydroamination with nitroarenes," Organic Chemistry, Science Magazine, May 22, 2015, vol. 348, Issue 6237, pp. 886-892.
Jagadeesh, Rajenahally V., et al.—"Nanoscale Fe2O3-Based Catalysts for Selective Hydrogenation of Nitroarenes to Anilines," Science, New Series, vol. 342, No. 6162, Nov. 29, 2013, pp. 1073-1076.
Jagadeesh, Rajenahally V., et al.—"Nitrogen-Doped Graphene-Activated Iron-Oxide-Based Nanocatalysts for Selective Transfer Hydrogenation of Nitroarenes," ACS Catalysis Letters, 2015, 5, pp. 1526-1529.
Lin, Shu-Yi, et al.,—"A Simple Strategy for Prompt Visual Sensing by Gold Nanoparticles: General Applications of Interparticle Hydrogen Bonds," Angewandte Chemie Int. Ed., 2006, 45, pp. 4948-4951.
Liu, Ruili, et al.—"Bottom-Up Fabrication of Photoluminescent Graphene Quantum Dots with Uniform Morphology," Journal of the American Chemical Society, 2011, 133, pp. 15221-15223.
Luo, Peihui, et al.—"Graphene quantum dots/Au hybrid nanoparticles as electrocatalyst for hydrogen evolution reaction," Chemical Physics Letters, 641, 2015, pp. 29-32.
Peng, Juan, et al.—"Graphene Quantum Dots Derived from Carbon Fibers," Nano Letters, 2012, 12, pp. 844-849.
Perreault, Francois, et al.—"Thin-Film Composite Polyamide Membranes Functionalized with Biocidal Graphene Oxide Nanosheets," Environmental Science and Technology Letters, 2014, 1, pp. 71-76.
Pian, Xue-Tao, et al.—"Pillared Nanocomposite TiO2/Bi-Doped Hexaniobate with Visible-Light Photocatalytic Activity," The Journal of Physical Chemistry, C 2011, 115, 6531-6539.
Tang, Qunwei, et al.—"High conducting multilayer films from poly(sodium styrenesulfonate) and graphite nanoplatelets by layer-by-layer self-assembly," Polymer 49, 2008, pp. 5329-5335.
Xiao, Fang-Xing, et al.—"Layer-by-Layer Self Assembly of CdS Quantum Dots/Graphene Nanosheets Hybrid Films for Photoelectrochemical and Photocatalytic Applications," Journal of the American Chemical Society, 2014, 136, pp. 1559-1569.
Yan, Xin, et al.—"Large, Solution-Processable Graphene Quantum Dots as Light Absorbers for Photovoltaics," Nano Letters, 2010, 10, pp. 1869-1873.
Yeh, Te-Fu, et al.—"Nitrogen-Doped Graphene Oxide Quantum Dots as Photocatalysts for Overall Water-Splitting under Visible Light Illumination," Materials Views, Advanced Materials, 2014, 26, pp. 3297-3303.
Zeng, Zhiping, et al.—"Unraveling the cooperative synergy of zero-dimensional graphene quantum dots and metal nanocrystals enabled by layer-by-layer assembly," The Royal Society of Chemistry, Journal of Materials Chemistry A, 2018, 6, pp. 1700-1713.
Zhang, Nan, et al.—"Waltzing with the Versatile Platform of Graphene to Synthesize Composite Photocatalysts," Chemical Reviews, ACS Publications, 2015, 115, pp. 10307-10377.
Zhang, Zhipan, et al.—"Graphene quantum dots: an emerging material for energy-related applications and beyond," The Royal Society of Chemistry, Energy & Environmental Science, 2012, 5, pp. 8869-8890.
Achadu et al. "The Interaction between graphene quantum dots grafted with polythyleneimine and Au@Ag nanoparticles: Application as a fluorescene "turn-on" nanoprobe," Journal of Photochemistry Photobiology A: Chemistry, 324, 2016, pp. 96-105.
Albanese et al. "Effect of Gold Nanoparticle Aggregation on Cell Uptake and Toxicity," ACS Nano 2011, vol. 5, No. 7, pp. 5478-5489.
Decher "Fuzzy Nanoassemblies: Toward Layered Polymeric Multicomposites," Science, Aug. 29, 1997, vol. 277, pp. 1232-1237.
Luo et al. "Graphene quantum dots/Au hybrid nanoparticles as electrocatalyst for hydrogen evolution reaction," Chemical Physics Letters, vol. 641, Oct. 2015, pp. 29-32.
Ponomarenko et al. "Chaotic Dirac Billiard in Graphene Quantum Dots," Science, Apr. 18, 2008, vol. 320, No. 5874, pp. 356-358.
Wang et al. "Aggregation-Free Gold Nanoparticles in Ordered Mesoporous Carbons: Toward Highly Active and Stable Heterogeneous Catalysts," J. Am. Chem. Soc., Jul. 18, 2013, vol. 135, No. 32, pp. 11849-11860.
Xia et al. "Recent progress on graphene-based hybrid electrocatalysts," Materials Horizons, Mar. 31, 2014, vol. 1, pp. 379-399.
Zeng et al. "Graphene Oxide Quantum Dots Covalently Functionalized PVDF Membrane with Significantly-Enhanced Bactericidal and Antibiofouling Performances," Scientific Reports, 6:20142, Feb. 2016, pp. 1-11.
Zhang et al. "Graphene quantum dots/gold electrode and its application in living cell H2O2 detection," Nanoscale, 2013, vol. 5, pp. 1816-1819.
International Search Report and the Written Opinion for International Application No. PCT/SG2017/050588 dated Feb. 28, 2018, 8 pages.

* cited by examiner

MULTI-LAYERED METAL-CARBON MATERIALS-BASED NANOARCHITECTURES

FIELD OF INVENTION

The invention relates to composite materials having one or more bilayers of metal nanocrystals and graphene quantum dots. Said materials may be particularly useful in a number of catalytic applications.

BACKGROUND

The listing or discussion of an apparently prior-published document in this specification should not necessarily be taken as an acknowledgement that the document is part of the state of the art or is common general knowledge.

The search for efficient catalysts for the selective oxidation or reduction of key industrial intermediates and for use in sustainable renewable energy conversion systems has been one of the top priorities for harnessing resources and energy in modern society. Recent years have witnessed the exploration of a large variety of nanomaterials for heterogeneous catalysis and electrocatalysis, which represent two broad key themes for resolving synthetic issues and energy issues.

Among the diverse nanomaterials under consideration, metal nanocrystals (NCs) are of particular note because they can perform as heterogeneous catalysts in selective organic transformations and in electrocatalysis for chemical-to-energy conversion by virtue of their unique catalytic properties, which include highly active surface atoms (e.g. see: Wu, X. C. et al., Chem Commun 2015, 51, 6318-6321; Yin, H. J. et al., Acs Nano 2012, 6, 8288-8297; Luo, P. H. et al., Chem Phys Lett 2015, 641, 29-32; Zhang, Y. et al., Nanoscale 2013, 5, 1816-1819; and Ran, X. et al., Chem Commun 2013, 49, 1079-1081). Nevertheless, a quintessential problem in utilizing metal NCs in the research fields identified above is their irreversible aggregation, which induces a substantial loss of the intrinsic surface properties of the nanocrystals, leading to a reduced nanoscale catalytic effect. To solve this problem, it is highly desirable to develop an effective strategy that preserves the active surface of metal NCs (Wang, S. et al., J Am Chem Soc 2013, 135, 11849-11860; Yan, H. et al., J Am Chem Soc 2015, 137, 10484-10487; Albanese, A. et al., Acs Nano 2011, 5, 5478-5489).

Graphene quantum dots (GQDs), a unique zero-dimensional (0D) carbon nanomaterial that is composed of a nanostructure analogous to graphene, have recently garnered tremendous research interest because of the remarkable electrical and chemical properties associated with quantum-confinement and edge effects of such GQDs (e.g. see: Ponomarenko, L. A. et al., Science 2008, 320, 356-358; and Lu, J. et al., Nat Nanotechnol 2011, 6, 247-252). In particular, compared with the widely-investigated 2D graphene, 0D GQDs have an ultra-small particle size (<10 nm) that results in many more oxygen-containing functional groups on the planar surface serving as active centers.

The exceptionally high conductivity, large specific surface area and various active sites of GQDs render it a desirable target for integration with metal NCs, thereby forming unique 0D/0D heterostructures. The combination of GQDs with metal NCs at nanoscale could provide several benefits, including boosting electron transport in metal NCs with the aid of GQDs at the interfacial domain, preserving catalytic stability of metal NCs, and other synergistic interactions.

Hybrid systems using metal NCs (e.g., Au, or Ag) with GQDs have been reported for creating catalytically and electrocatalytically active nanomaterials for a wide range of applications. For instance, Au/GQDs composites have been prepared by heating $HAuCl_4$ with GQDs and the resulting product exhibited excellent chemical catalytic activity for the selective oxidation of veratryl alcohol (Wu, X. C. et al., Chem Commun 2015, 51, 6318-6321), high electrocatalytic activity for hydrogen evolution reaction (Luo, P. H. et al., Chem Phys Lett 2015, 641, 29-32), and a good performance in $H_2O_2$ detection (Zhang, Y. et al., Nanoscale 2013, 5, 1816-1819). Ag/GQDs composites have been disclosed for use as turn-on fluorescent nanoprobes, providing ultrasensitive and selective detection of prostate specific antigens (Pei, H. M. et al., Biosens Bioelectron 2015, 74, 909-914), biothiols (Achadu, O. J. et al., J Photoch Photobio A 2016, 324, 96-105) and iodide (Xu, X. H. et al., Nanocomposite. Anal Sci 2015, 31, 787-791). Despite these intense endeavors, the rational fabrication and systematic exploration of the promising applications of M-GQD heterostructures, such as in selective organic transformation and in electrocatalytic methanol oxidation have yet to be reported. The synthetic approaches to prepare M/GQDs nanocomposites disclosed to date are mainly centered on slurry systems in which constituent ingredients were randomly mixed. This makes it difficult to exert a tunable control over the components and this in turn makes it difficult to fabricate well-defined M/GQDs (0D/0D) hybrid nanostructures, resulting in poor interfacial contact between the components. Moreover, the disclosed approaches are complicated and environmentally-unfriendly.

Layer-by-Layer (LbL) self-assembly is a bottom-up fabrication technique that has been reported by Decher, G. et al., Science 1997, 277, 1232-1237; Xiao, F. X. et al., J Am Chem Soc 2015, 137, 10735-10744.

SUMMARY OF INVENTION

The inventors have surprisingly found a composite material that overcomes a number of the issues mentioned above. Thus, in a first aspect of the invention, there is provided a multilayered composite thin film material comprising:
  a substrate having a positively-charged surface;
  a first bilayer material comprising:
    a layer of metal nanocrystal particles, each particle having a negatively charged surface, where the metal is selected from the group consisting of Ru, Rh, Os, Ir, Pd, Au, Ag and Pt, and the particles are attached to the substrate surface by charge attraction; and
    a coating layer of graphene quantum dots, each graphene quantum dot having a positively charged surface and attached to the layer of metal nanocrystal particles by charge attraction; and
  a 0 to $n^{th}$ additional bilayers comprising:
    a layer of metal nanocrystal particles, each particle having a negatively charged surface, where the metal is selected from the group consisting of Ru, Rh, Os, Ir, Pd, Au, Ag and Pt, and the particles are attached to the preceding layer of graphene quantum dots by charge attraction; and
    a coating layer of graphene quantum dots, each graphene quantum dot having a positively charged surface and attached to the layer of metal nanocrystal particles by charge attraction, where n is from 1 to 49.

In embodiments of the first aspect of the invention:

(a) n may be from 1 to 19, such as from 4 to 14, such as 9;

(b) the positively charged surface of the graphene quantum dots may be provided by covalently bonded moieties comprising an ammonium ion functional group;

(c) the graphene quantum dots may have a particle size of from 3 to 20 nm, such as from 4 to 10 nm, such as 5.6 nm, optionally wherein the particles have a uniform size of from 3 to 20 nm, such as from 4 to 10 nm, such as 5.6 nm;

(d) the graphene quantum dots may have a thickness of from about 0.7 to about 1.2 nm, or a thickness of from 1 to 2 layers of graphene;

(e) the graphene quantum dots may have a measured zeta potential of from +40 mV to +70 mV, such as +53.5 mV when measured using a pH profile of from pH 7 to 12;

(f) each layer of metal nanocrystal particles may comprise a metal selected from the group consisting of Pd, Au, Ag and Pt, such as Au, Ag and Pt;

(g) the negatively charged surface of the metal nanocrystals is provided by moieties comprising carboxylate ions;

(h) the metal nanocrystals may have an average diameter of from 3 nm to 20 nm, such as from 3.09 to 15 nm;

(i) the metal nanocrystals may have a measured zeta potential of from −30 mV to −60 mV when measured using a pH profile of from pH 6 to 12;

(j) the composite material may have an image-average current of from 20 to 500 pA, such as from 50 to 250 pA, such as from 100 to 180 pA as measured by conductive atomic force microscopy;

(j) the metal nanocrystals may be citrate-stabilized metal nanocrystals, optionally wherein the metal nanocrystals may be citrate-stabilized gold nanocrystals, n is 9 and the composite material has an image-average current of from 150 to 200 pA, such as 171.3 pA as measured by conductive atomic force microscopy;

(j) the metal nanocrystals may be:
(i) gold nanocrystals having an average particle size of from 12 to 17 nm (such as from 12.1 to 16.3 nm, such as 14.2 nm); and/or
(ii) silver nanocrystals having an average particle size of from 5 to 8 nm (such as from 5.77 to 7.17 nm, such as 6.47 nm); and/or
(iii) platinum nanocrystals having an average particle size of from 2 to 4 nm (such as from 2.49 to 3.69 nm, such as 3.09 nm);

(k) the substrate may be selected from one or more of the group consisting of fluorine-doped tin oxide, glass, silicon, indium tin oxide (ITO), and titanium (e.g. fluorine-doped tin oxide, glass, and silicon);

(l) the positively charged surface of the substrate may be provided by a polycationic polymer selected from the group consisting of polyethylenimine, poly(diallyldimethylammonium chloride) (PDDA), copolymers thereof, and blends thereof.

In a second aspect of the invention, there is provided a method of assembling the multilayer composite thin film material according to the first aspect of the invention and any technically sensible combination of its embodiments, comprising the steps of:

(a) providing a substrate having a positively charged surface;

(b) dipping the substrate into a first solution comprising negatively charged metal nanocrystals, subsequently washing and drying the dipped material to form a negatively charged surface of metal nanocrystals;

(c) dipping the product of step (b) into a second solution comprising positively charged graphene oxide quantum dots, subsequently washing and drying the dipped material to form a positively charged surface;

(d) optionally repeating steps (b) and (c) n times using the product of step (c) as the substrate;

(e) subjecting the product of step (c) or, when conducted, step (d) to an annealing step under heat and an inert atmosphere, wherein:

n is from 1 to 49; and the metal nanocrystals used in each step (b) are independently selected from the group consisting of Ru, Rh, Os, Ir, Pd, or, more particularly, Au, Ag and Pt.

In a third aspect of the invention, there is provided a method of catalysing an organic reaction comprising contacting one or more reagents for the organic reaction with the composite material according to according to the first aspect of the invention (and any technically sensible combination of its embodiments) and providing the conditions necessary to effect the organic reaction.

In embodiments of the third aspect of the invention:

(a) the method may be the catalytic reduction of aromatic nitro compounds to aromatic amine compounds in the presence of a reducing agent, optionally wherein the reducing agent is sodium borohydride; or (b) the method may be the oxidation of methanol in an electrocatalytic reaction to produce carbon dioxide, optionally wherein the method involves placing a working electrode comprising the composite material according to the first aspect of the invention (and any technically sensible combination of its embodiments) into an electrolyte solution containing methanol under an inert atmosphere.

In a fourth aspect of the invention, there is provided a device suitable for photodetection and/or energy harvesting comprising a composite material according to the first aspect of the invention and any technically sensible combination of its embodiments. In certain embodiments, the composite material may be provided as part of an electrode.

In a fifth aspect of the invention, there is provided a method of energy harvesting involving the steps of:

(a) providing a light-transparent device comprising a working electrode that comprises a composite material according to the first aspect of the invention and any technically sensible combination of its embodiments, at least one other electrode as a counter electrode and an electrolyte;

(b) irradiating the device with light to generate a photocurrent; and (c) converting water to hydrogen and oxygen.

DRAWINGS

Certain embodiments of the present disclosure are described more fully hereinafter with reference to the accompanying drawings.

FIG. 1. Schematic illustration for LbL assembly of $(M/GQDs)_n$ (M=Au, Ag, Pt; n=1, 5, 10, 15) multilayer composite thin films as active catalysts for selective aromatic nitro compound reduction and electrochemical methanol oxidation under ambient conditions.

Figure 2:
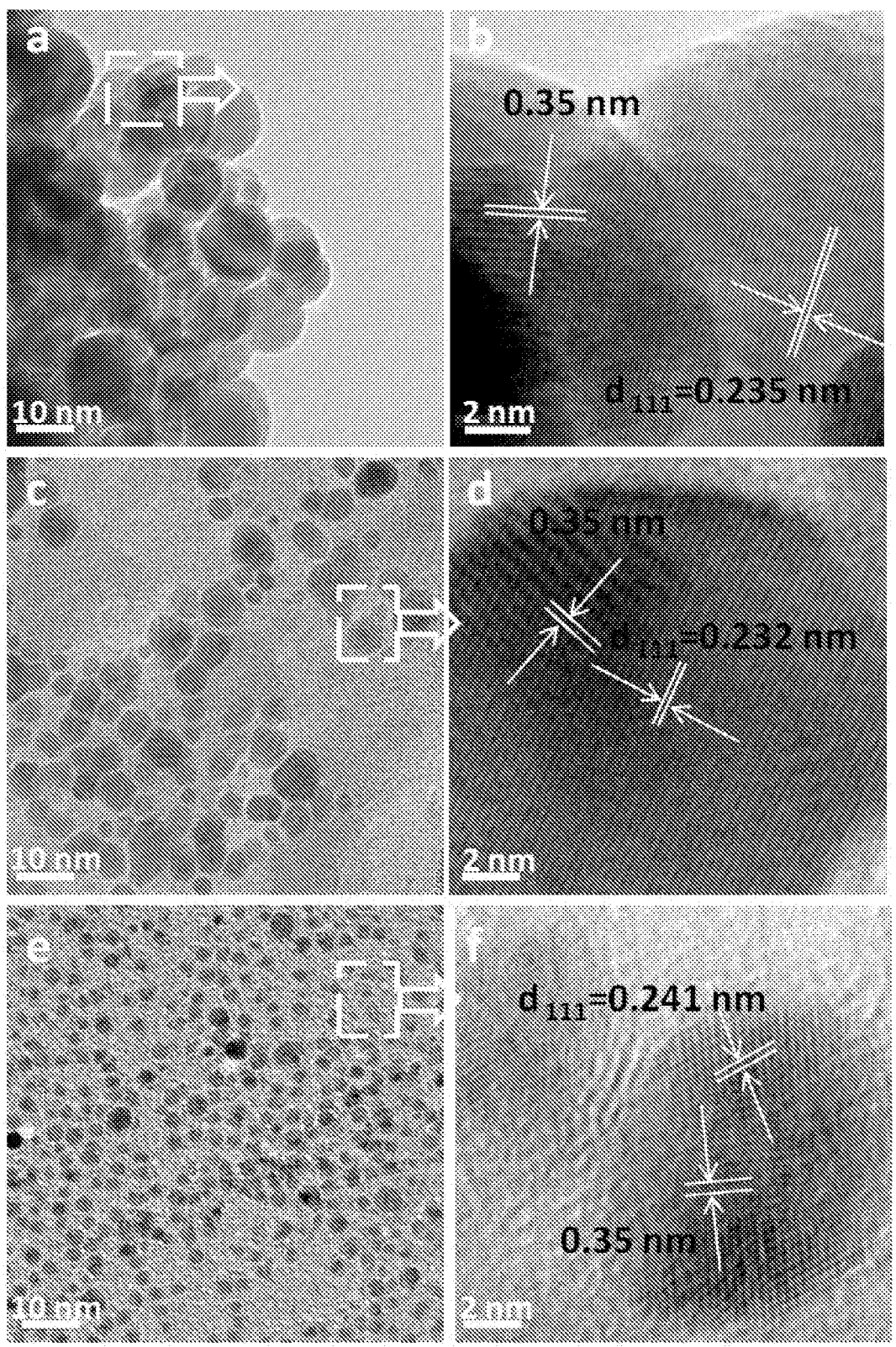

FIG. 2. TEM and corresponding HRTEM images of (a & b) $(Au/GQDs)_{10}$, (c & d) $(Ag/GQDs)_{10}$, (e & f) $(Pt/GQDs)_{10}$ multilayer composite films.

Figure 3:
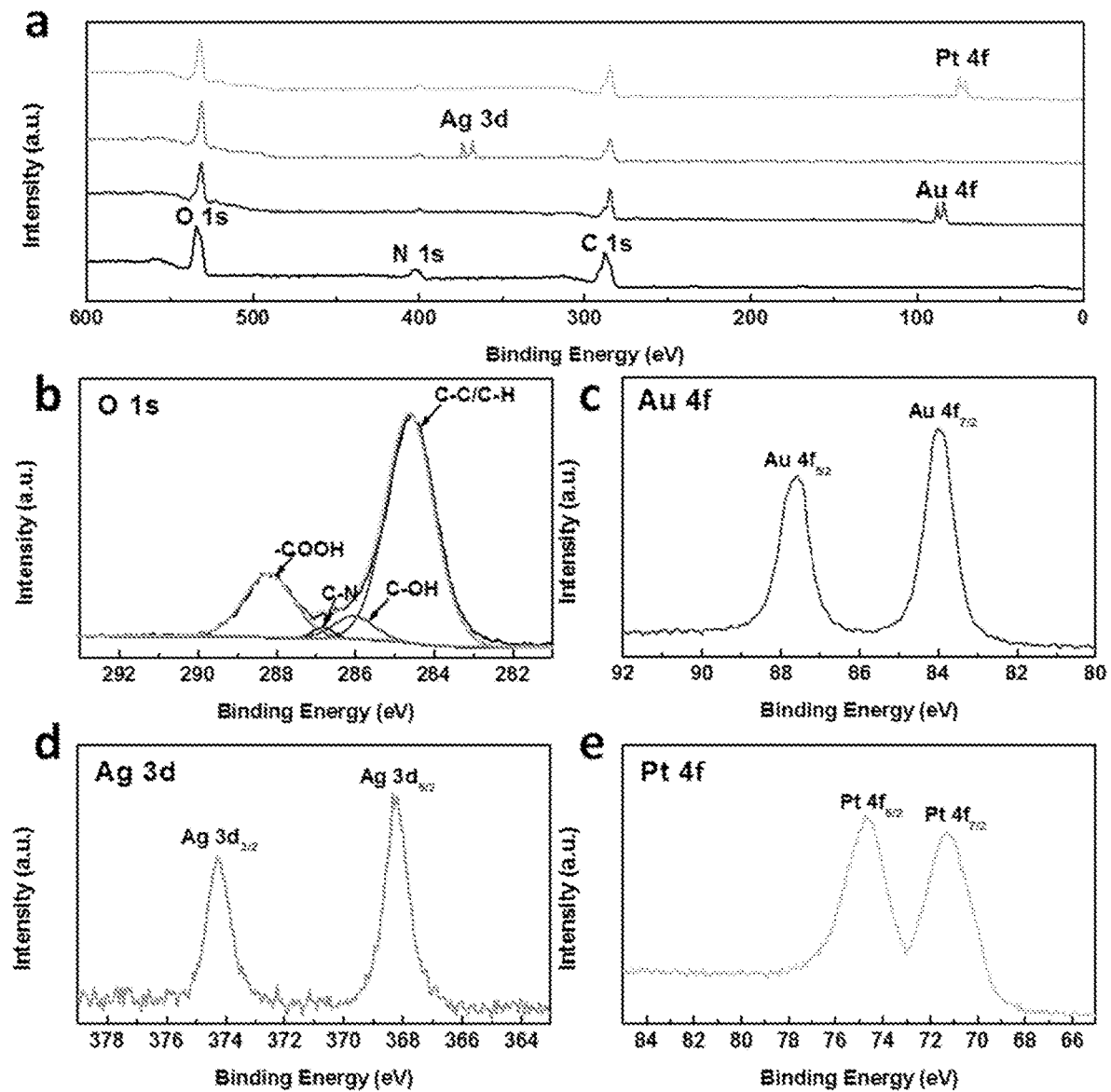

FIG. 3. (a) XPS survey spectra of modified $GQDs-NH_3^+$ (bottom spectra) and $(M/GQDs)_n$ (M=Au, Ag, Pt; as indicated in figure) multilayer composite thin films and high-resolution spectra of (b) C 1s, (c) Au 4f for $(Au/GQDs)_{10}$ film, (d) Ag 3d, and (e) Pt 4f for (Ag/GQDs)$_{10}$, and (Pt/GQDs)$_{10}$ films, respectively.

Figure 4:
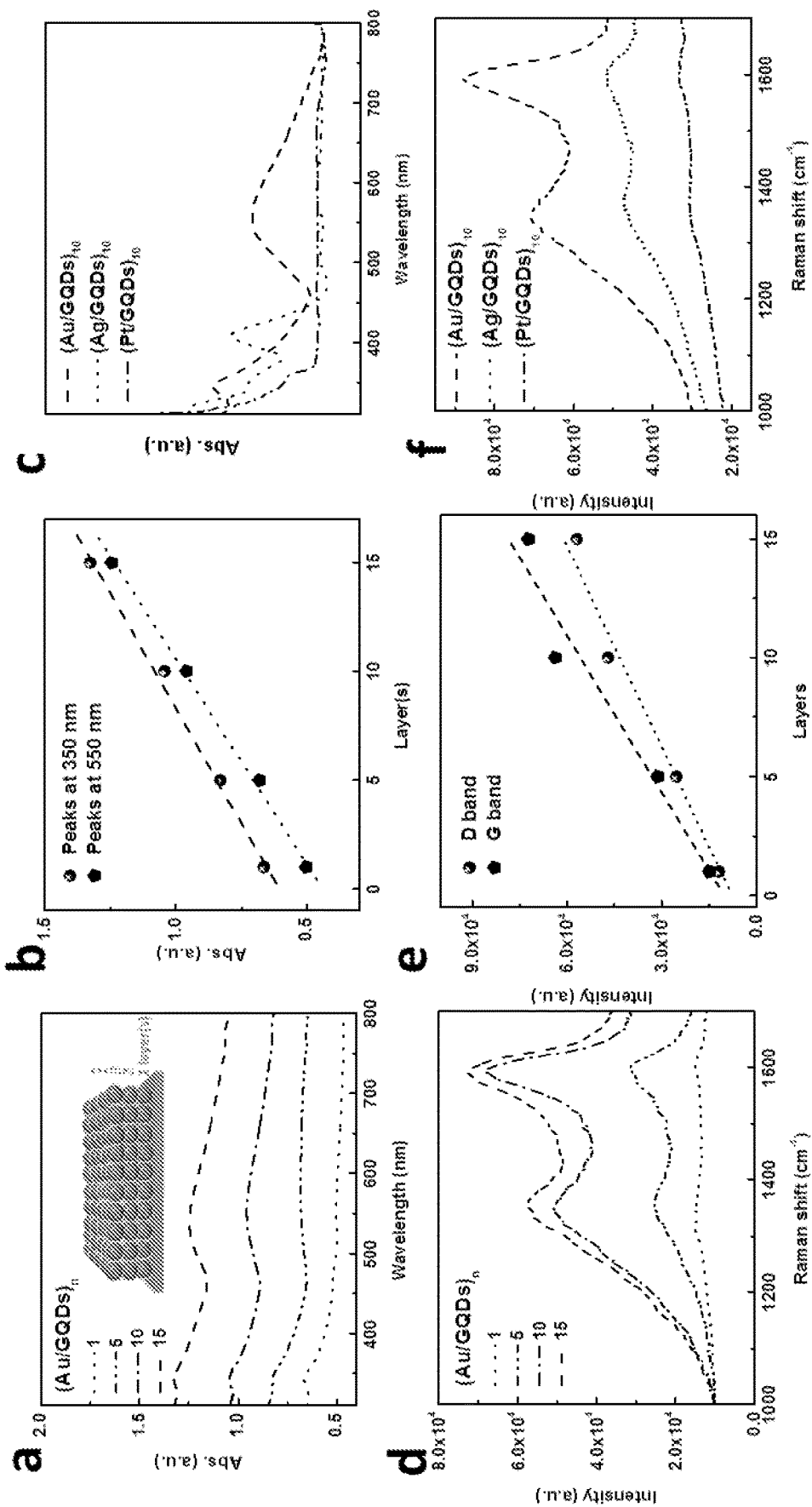

FIG. 4. (a) UV-vis diffuse reflectance spectra (DRS) of (Au/GQDs)$_n$ (n=1, 5, 10, 15) multilayer thin films, (b) peak intensity at 355 and 530 nm as a function of assembly cycle, and (c) DRS results of (M/GQDs)$_{10}$ (M=Au, Ag, Pt) multilayer thin films. (d) Raman spectra of (Au/GQDs)$_n$ (n=1, 5, 10, 15) multilayer thin films, (e) peak intensity of D and G bands as a function of assembly cycle, and (f) Raman spectra of (M/GQDs)$_{10}$ (M=Au, Ag, Pt) multilayer thin films.

Figure 5:
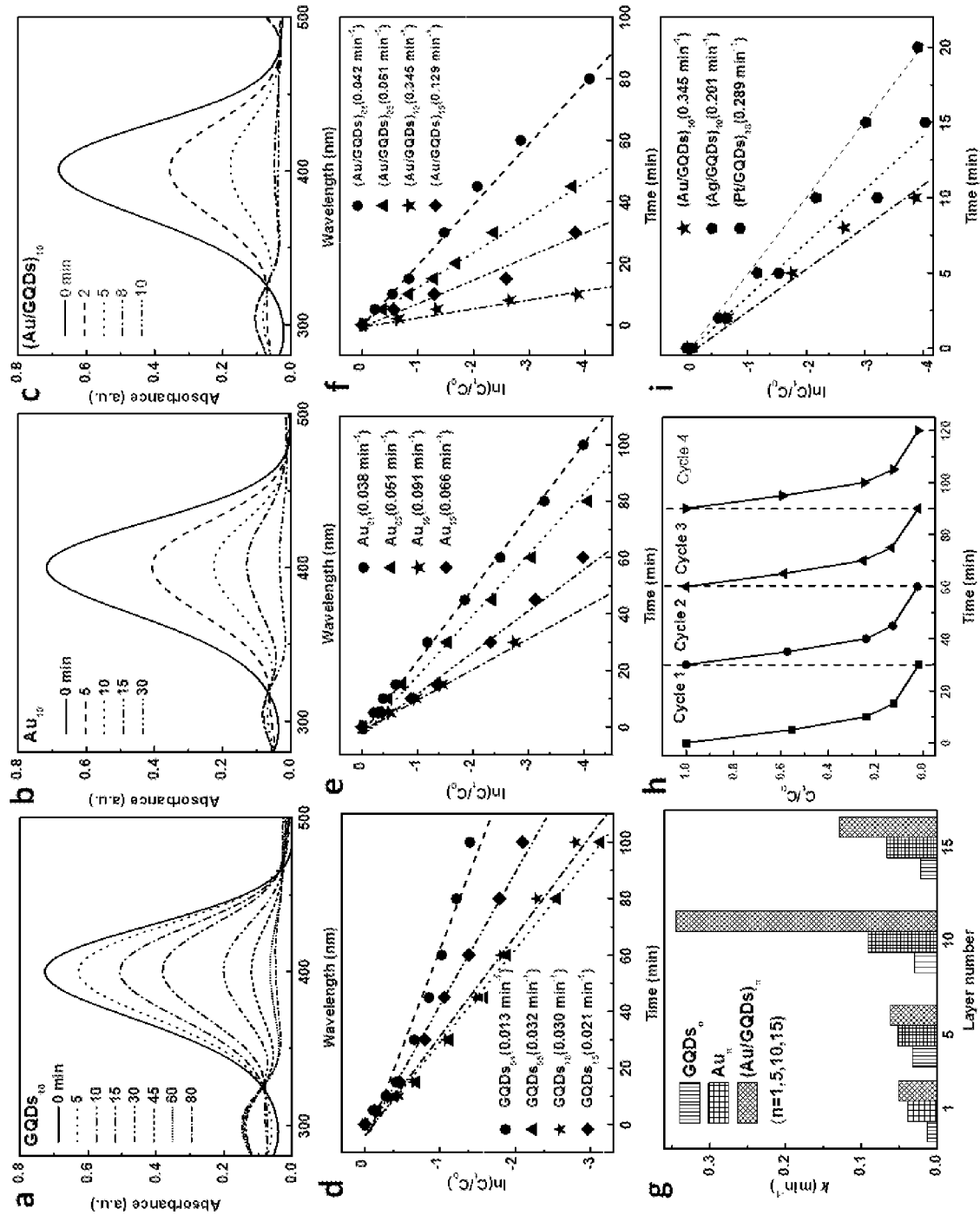

FIG. 5. (a-c) Time-dependent UV-vis absorption spectra for catalytic reduction of 4-NP to 4-AP over (a) (GQDs)$_{10}$, (b) (Au)$_{10}$, and (c) (Au/GQDs)$_{10}$ multilayer composite films. Plots of In(C$_t$/C$_0$) versus reaction time for reduction of 4-NP over (d) (GQDs)$_n$, (e) (Au)$_n$, and (f) (Au/GQDs)$_n$ films with an excess amount of NaBH$_4$ in aqueous media at ambient conditions by monitoring the decreased peak intensity of 4-NP at 400 nm. (g) Comparison of the reaction rate constants of different multilayer films. (h) Recycled catalytic reduction reactions over (Au/GQDs)$_{10}$ multilayer films. (i) Comparison results of catalytic reduction performances over (M/GQDs)$_{10}$ (M=Au, Ag, Pt) multilayer films with the same assembly layer.

Figure 6:
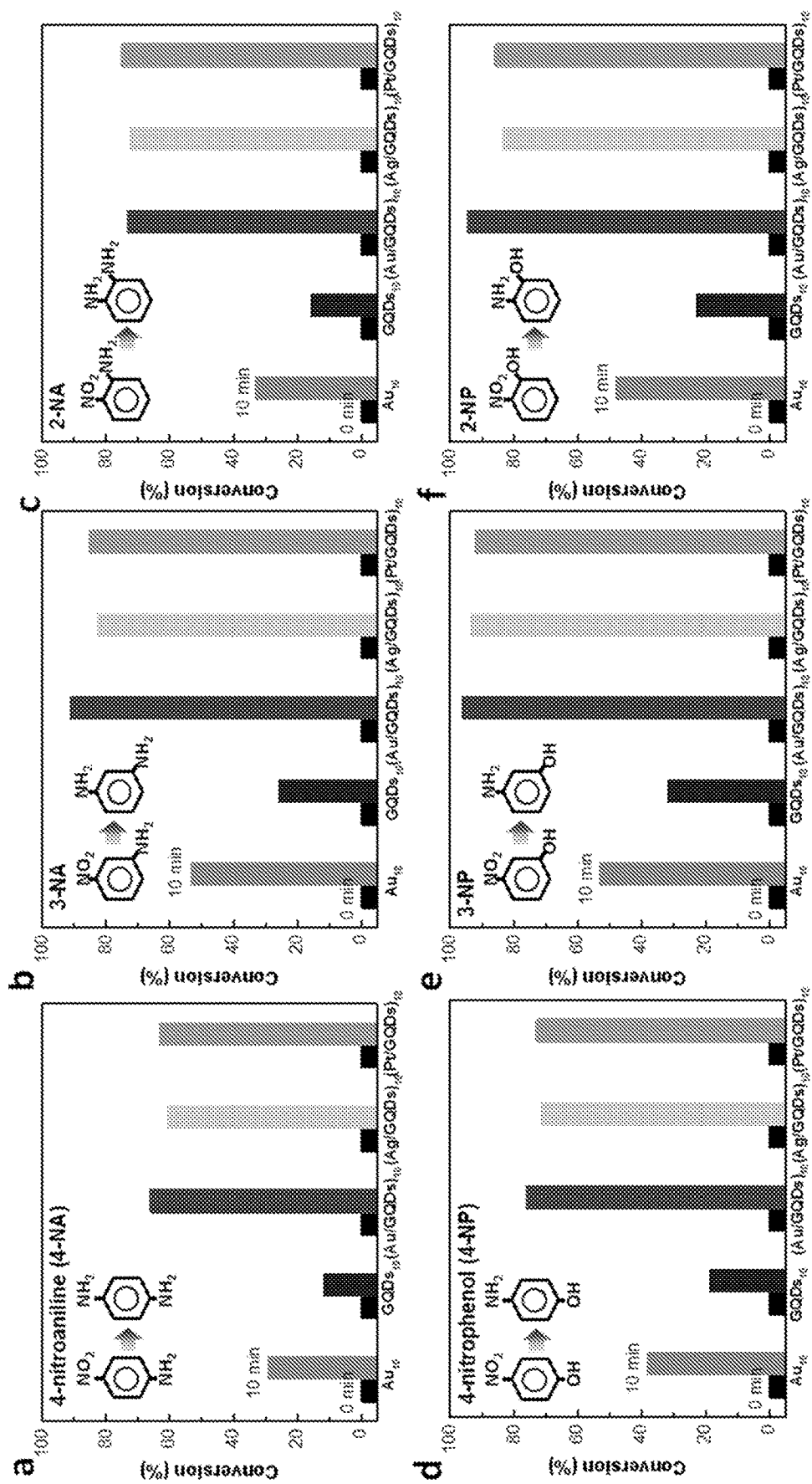

FIG. 6. Selective catalytic reduction of a series of aromatic nitro compounds including (a) 4-NA, (b) 3-NA, (c) 2-NA, (d) 4-NP, (e) 3-NP, and (f) 2-NP over (Au)$_{10}$, (GQDs)$_{10}$, (Au/GQDs)$_{10}$, (Ag/GQDs)$_{10}$, and (Pt/GQDs)$_{10}$ multilayer thin films for the same reaction time at ambient conditions.

Figure 7:
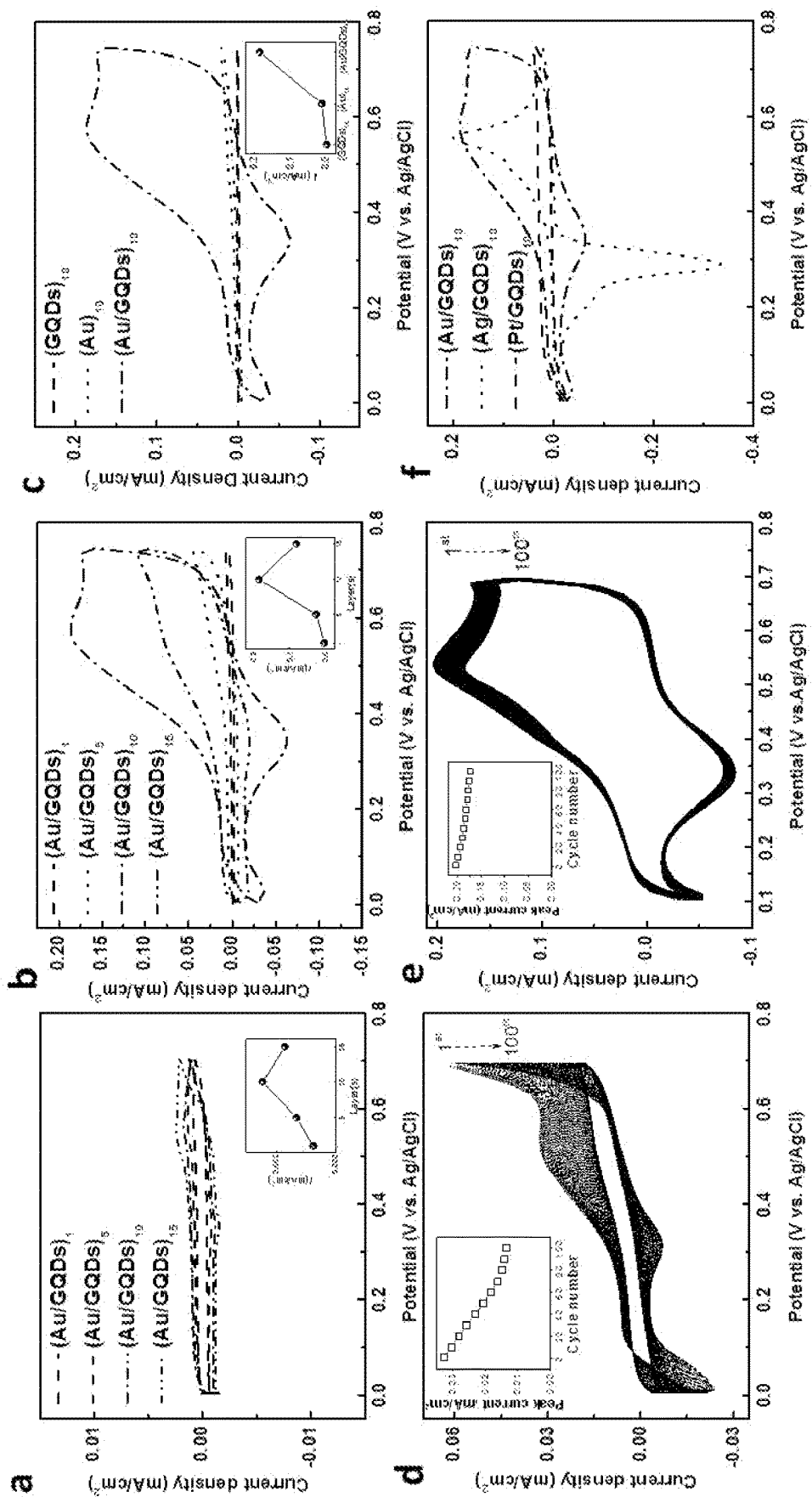

FIG. 7. Electro-catalytic oxidation performance of (M/GQDs)$_n$ (M=Au, Ag, Pt; n=1, 5, 10, 15) hybrid films. Cyclic voltammograms (CV) of (Au/GQDs)$_n$ (n=1, 5, 10, 15) hybrid films measured in 0.10 M KOH without methanol (a) and with 1.0 M methanol (b). (c) Cyclic voltammograms (CV) of GQDs$_{10}$, Au$_{10}$, and (Au/GQDs)$_{10}$ hybrid film measured in 0.10 M KOH with 1.0 M methanol. CV results of: (d) (Au)$_{10}$; (e) (Au/GQDs)$_{10}$ films; and (f) (M/GQDs)$_{10}$ (M=Au, Ag, Pt) multilayer thin films under the same experimental conditions.

Figure 8:
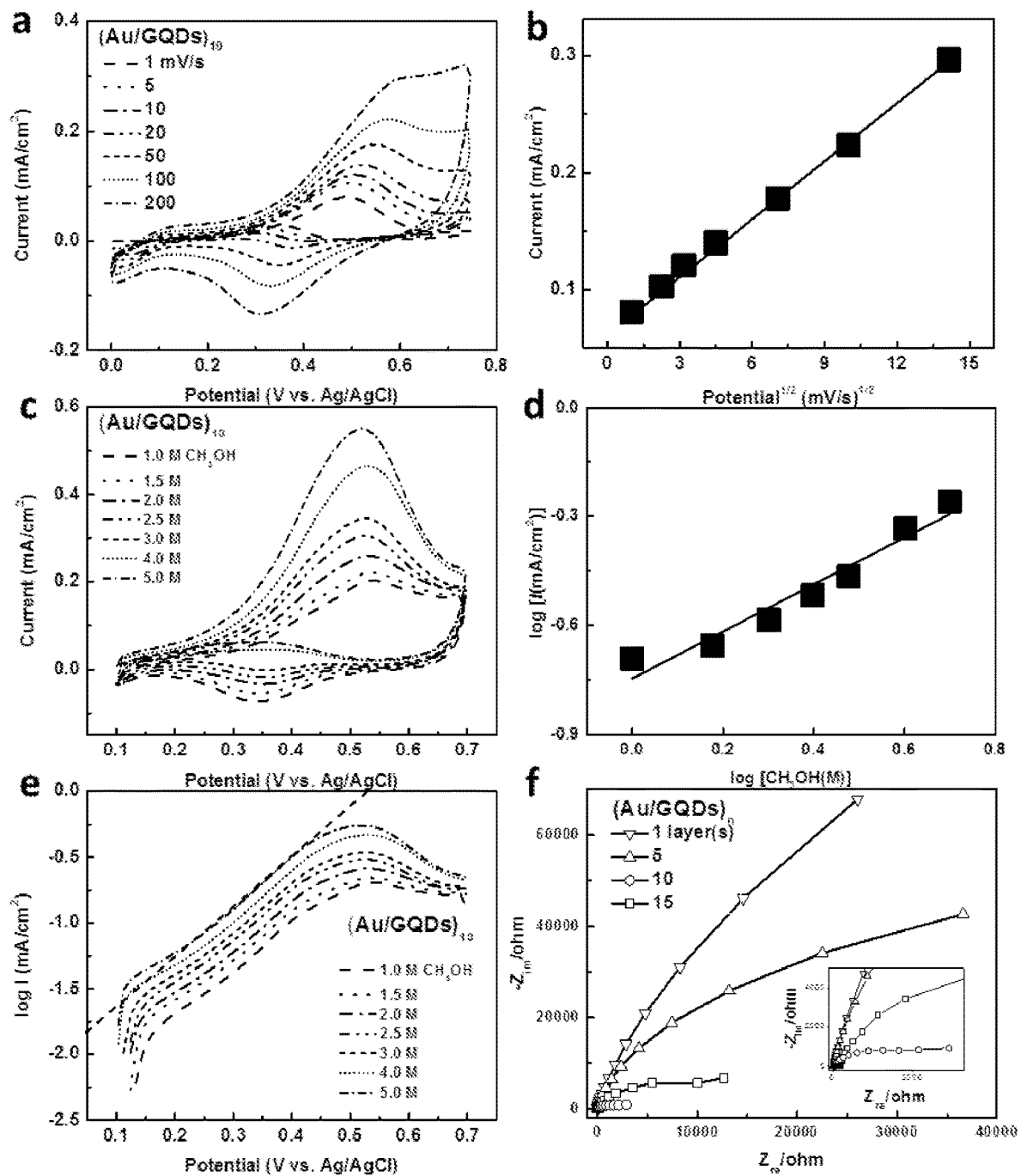

FIG. 8. (a) CV results of (Au/GQDs)$_{10}$ multilayer thin film measured in 0.10 M KOH with 1.0 M methanol in a saturated N$_2$ atmosphere with varying scan rates and (b) corresponding linear correlation of anodic peak current as a function of the square root of scan rates. (c) CV results of (Au/GQDs)$_{10}$ multilayer thin film with different methanol concentrations, (d) plots of log I (I is anodic peak current) vs. log(CCH$_3$OH) with different methanol concentrations, (e) Tafel plots with a representative linear fit, and (f) Nyquist plots of impedance for (Au/GQDs)$_n$ (n=1, 5, 10, 15) multilayer thin films measured in 0.10 M KOH with 1.0 M CH$_3$OH in a saturated N$_2$ atmosphere at a scan rate of 20 mV/s.

Figure 9:
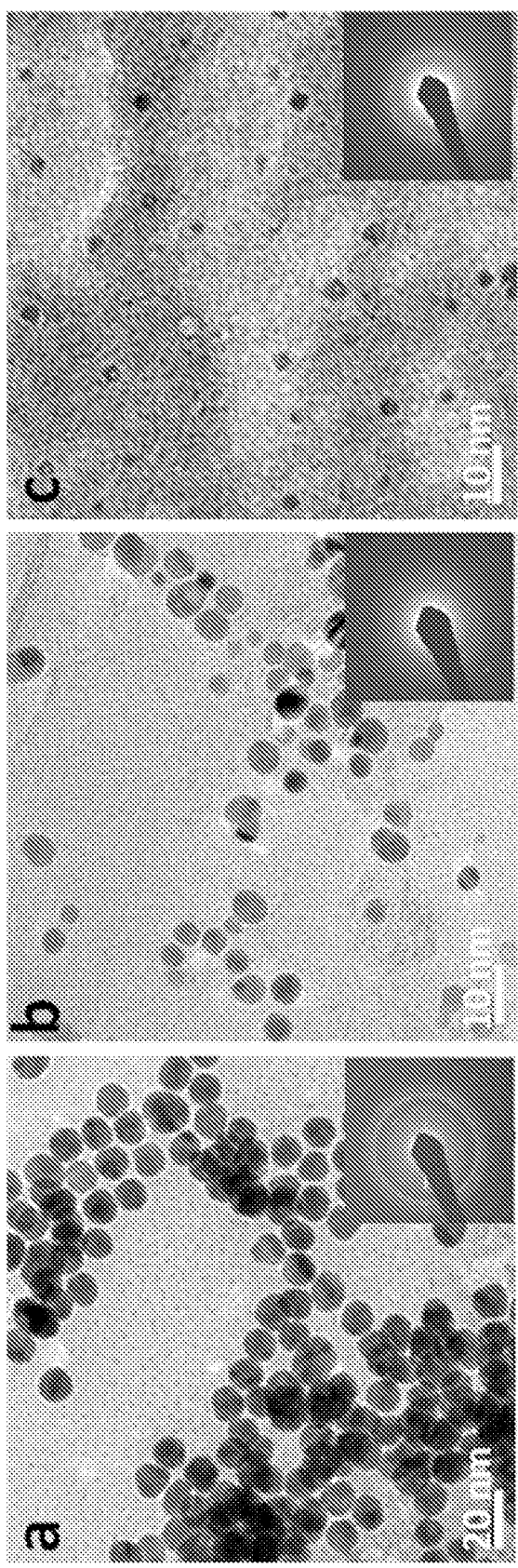
Figure 9:
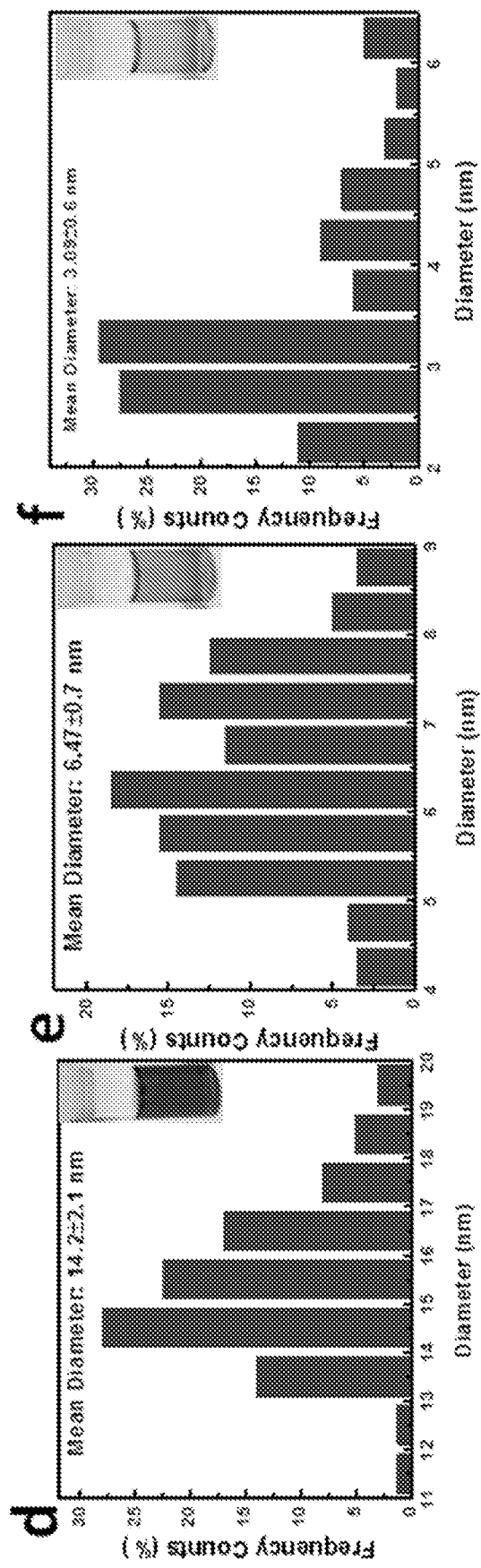

FIG. 9. (a-c) TEM images of citrate-stabilized (a) Au, (b) Ag, and (c) Pt NCs with corresponding SAED patterns in the inset. (d-f) The mean diameter histogram of (d) Au, (e) Ag, (f) Pt NCs.

Figure 10:
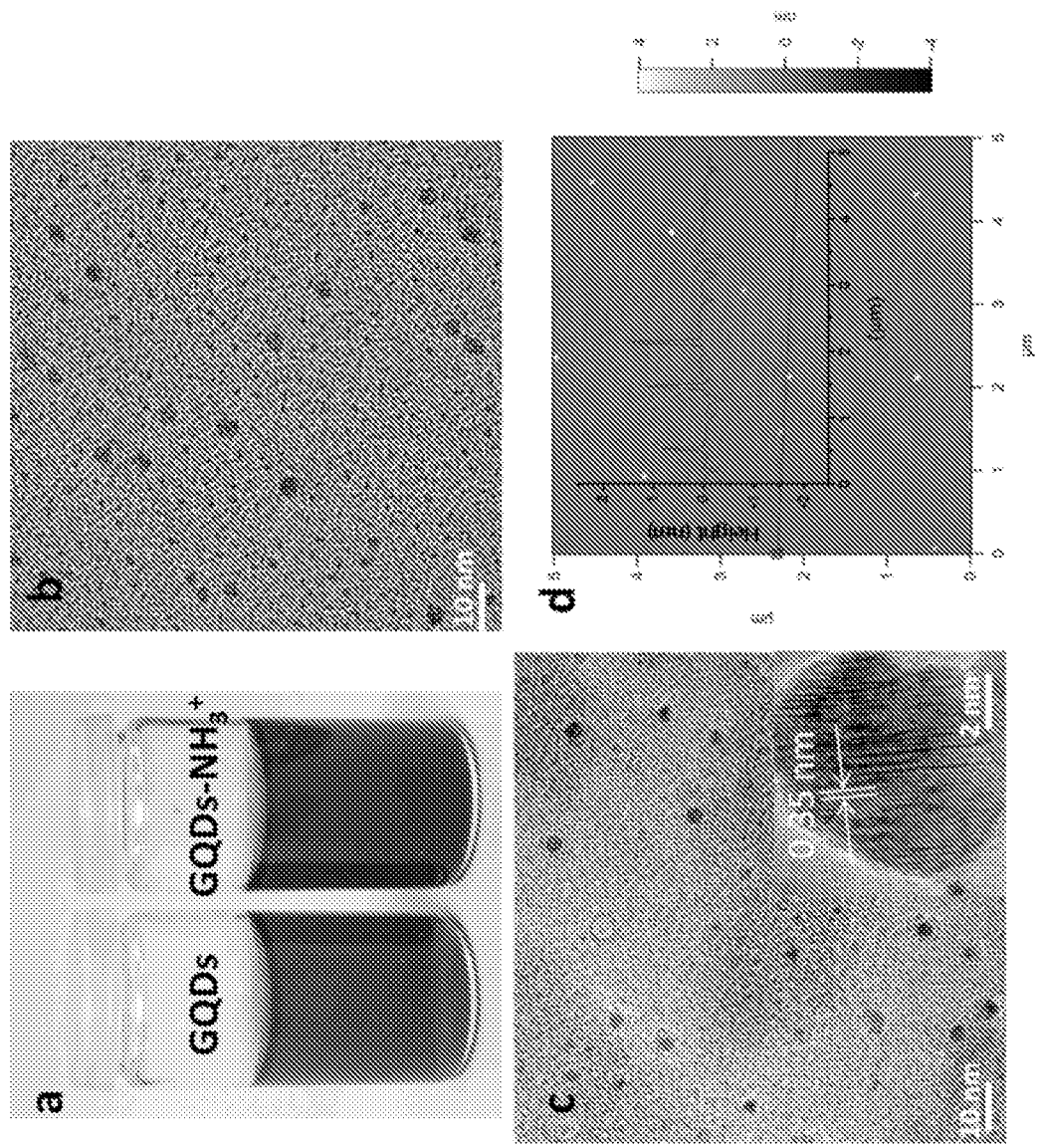

FIG. 10. (a) Digital photo of GOQDs and GOQDs-NH$_3^+$ aqueous solution. (b) TEM image of GOQDs. (c) TEM image of GOQDs-NH$_3^+$ with a high-resolution TEM image. (d) AFM image of GOQDs-NH$_3^+$ with the height profile along the line.

Figure 11:
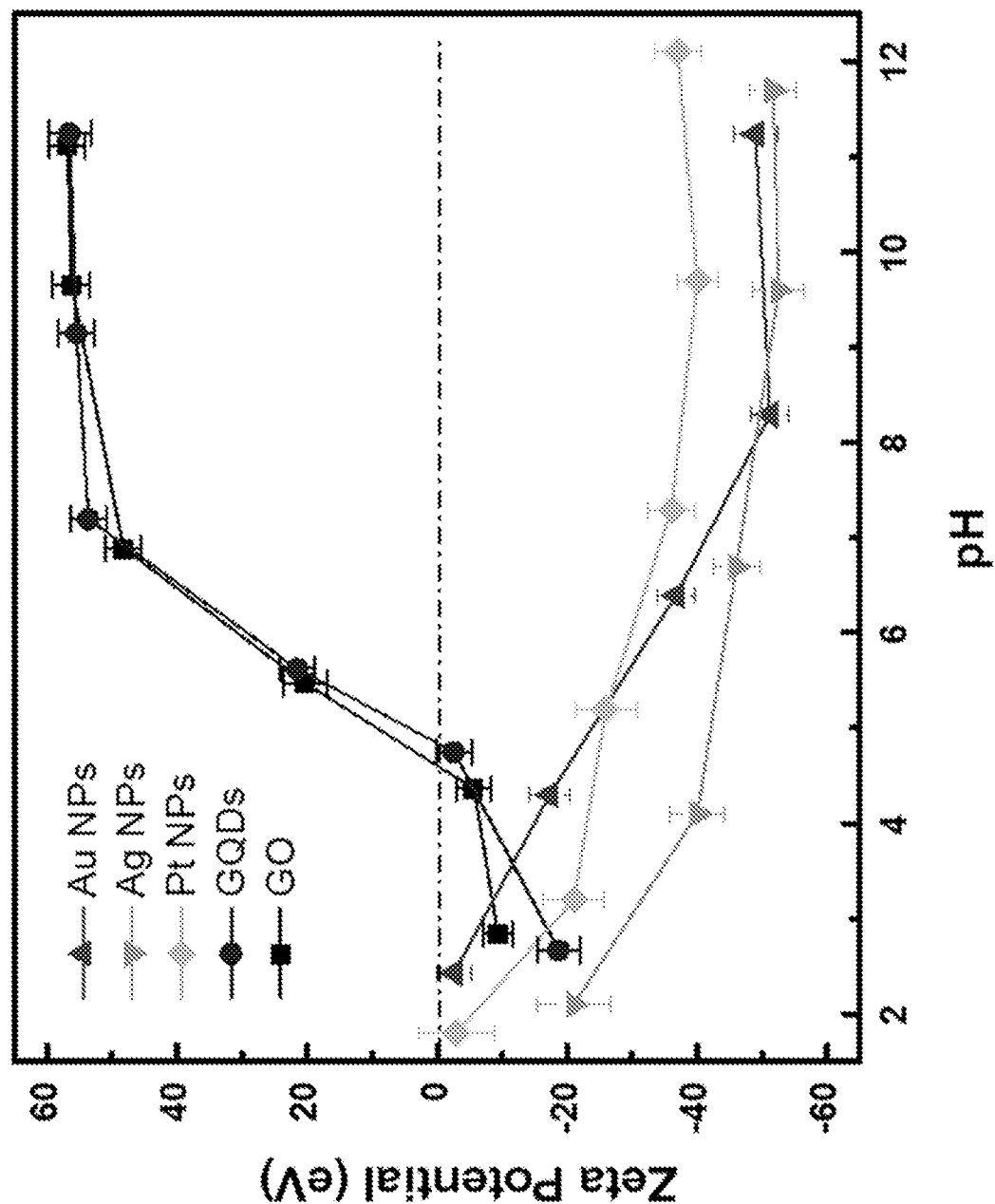

FIG. 11. Zeta potential of Au, Ag, Pt NPs (nanoparticles/nanocrystals) and GOQDs, GO with a function of pH value.

Figure 12:
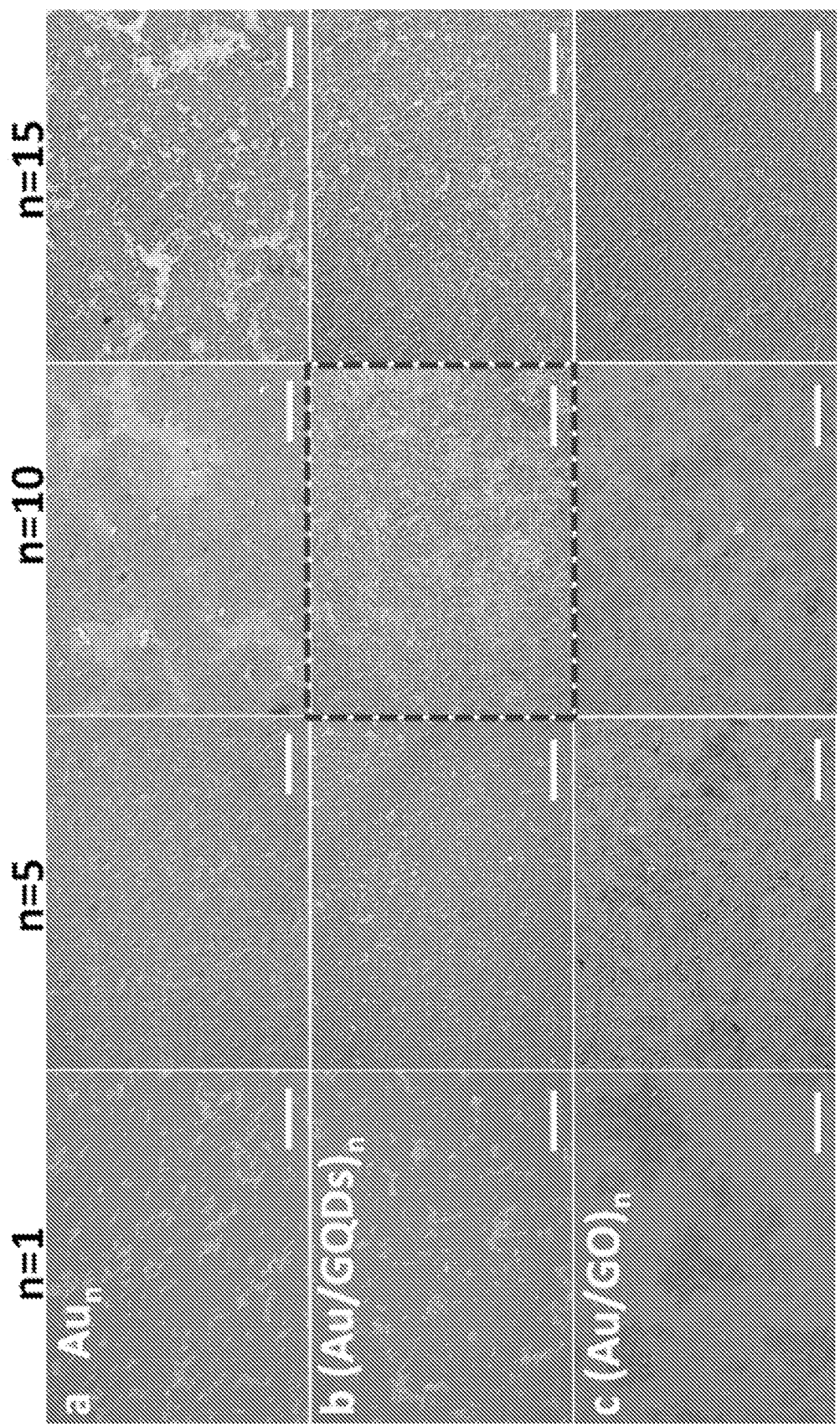

FIG. 12. SEM images of (a) Au$_n$, (b) (Au/GQDs)$_n$, and (c) (Au/GO)$_n$ (n=1, 5, 10, 15) thin films, scale bar is 2 μm.

Figure 13:
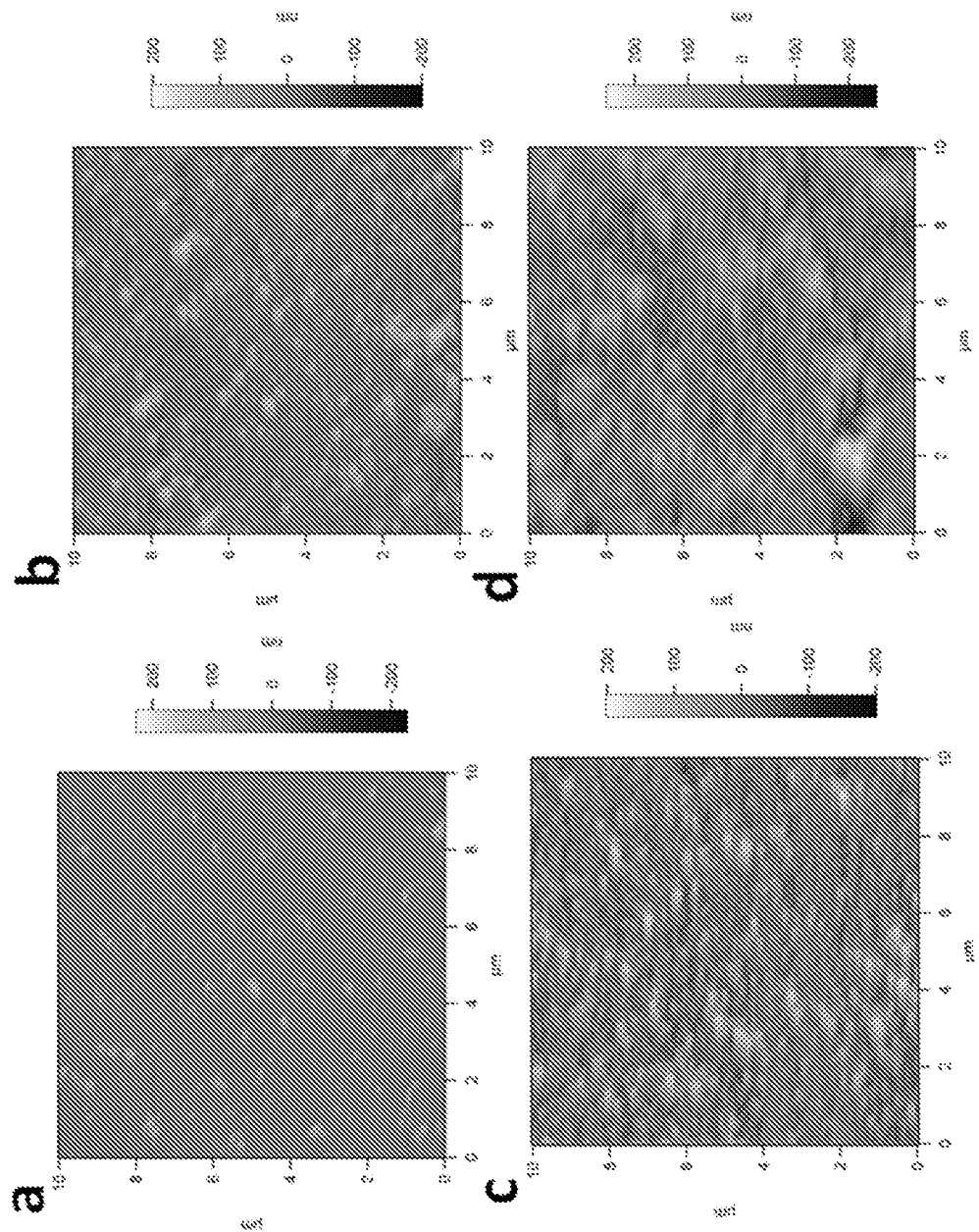

FIG. 13. AFM images of (Au/GQDs)$_n$ hybrid thin film: (a) n=1; (b) n=5; (c) n=10; (d) n=15.

Figure 14:
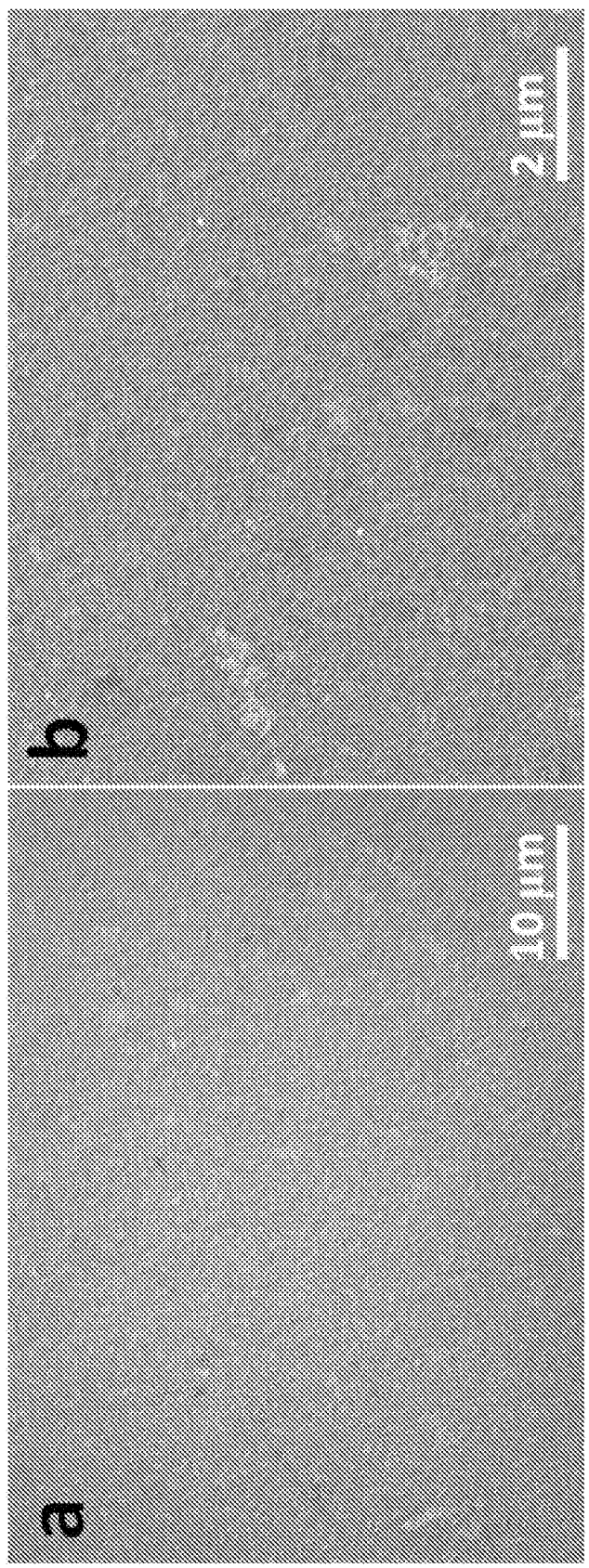

FIG. 14. SEM images of (Ag/GQDs)$_{10}$ (a), and (Pt/GQDs)$_{10}$ (b) hybrid thin film.

Figure 15:
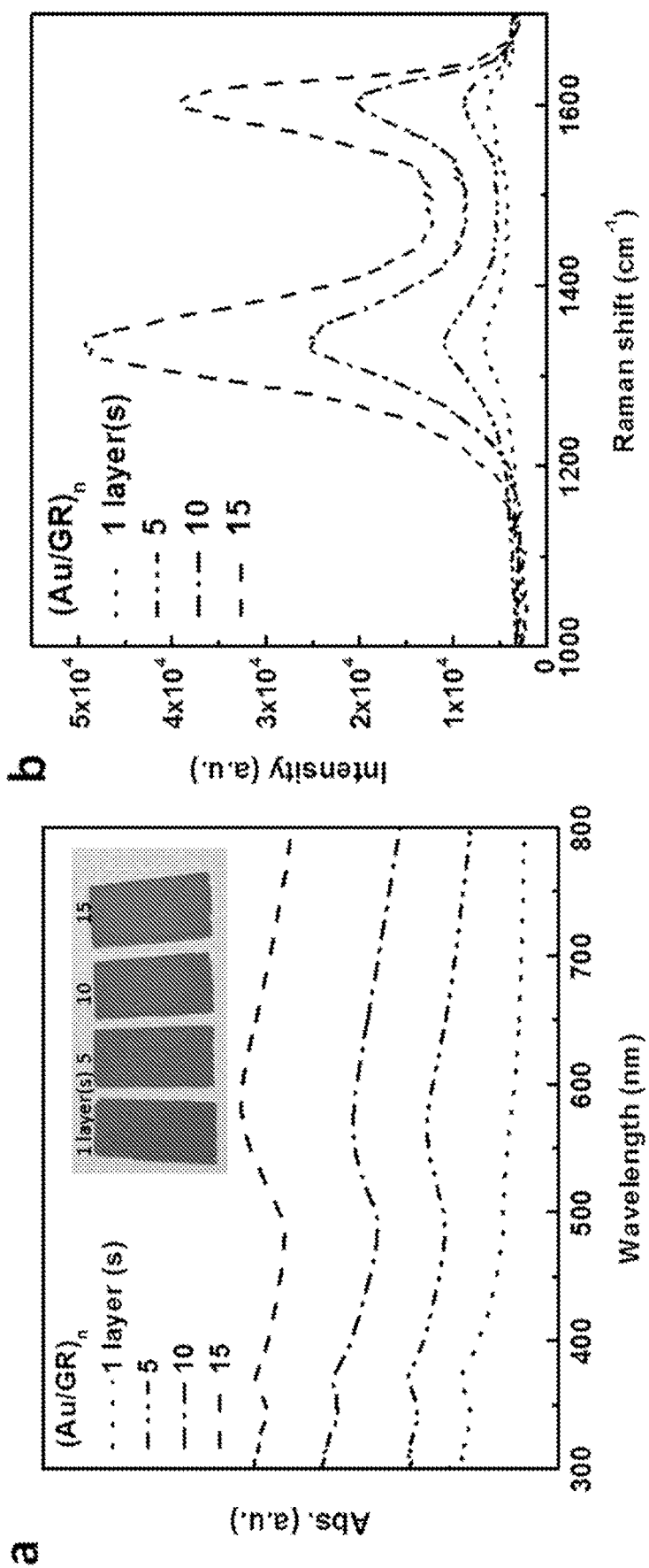

FIG. 15. (a) UV/vis absorbance spectra and (b) Raman spectra of (Au/GR)$_n$ (n=1, 5, 10, 15).

Figure 16:
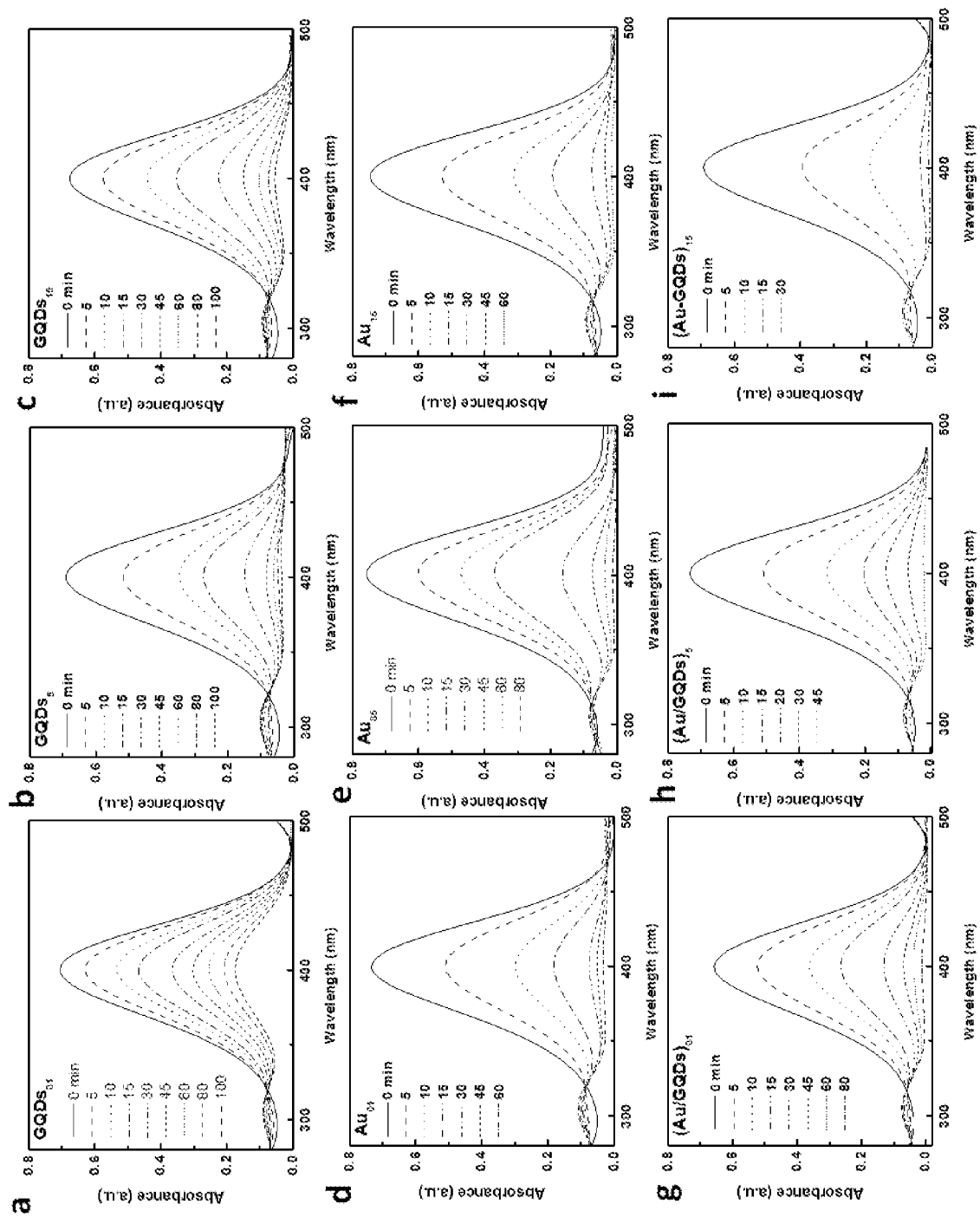

FIG. 16. Time-dependent UV/vis absorption spectra for the reduction of 4-nitrophenol over (a) GQDs$_{01}$, (b) GQDs$_{05}$, (c) GQDs$_{15}$, (d) Au$_{01}$, (e) Au$_{15}$, (f) Au$_{15}$, (g) (Au/GQDs)$_{01}$, (h) (Au/GQDs)$_{05}$, and (i) (Au/GQDs)$_{15}$ thin films catalysts.

Figure 17:
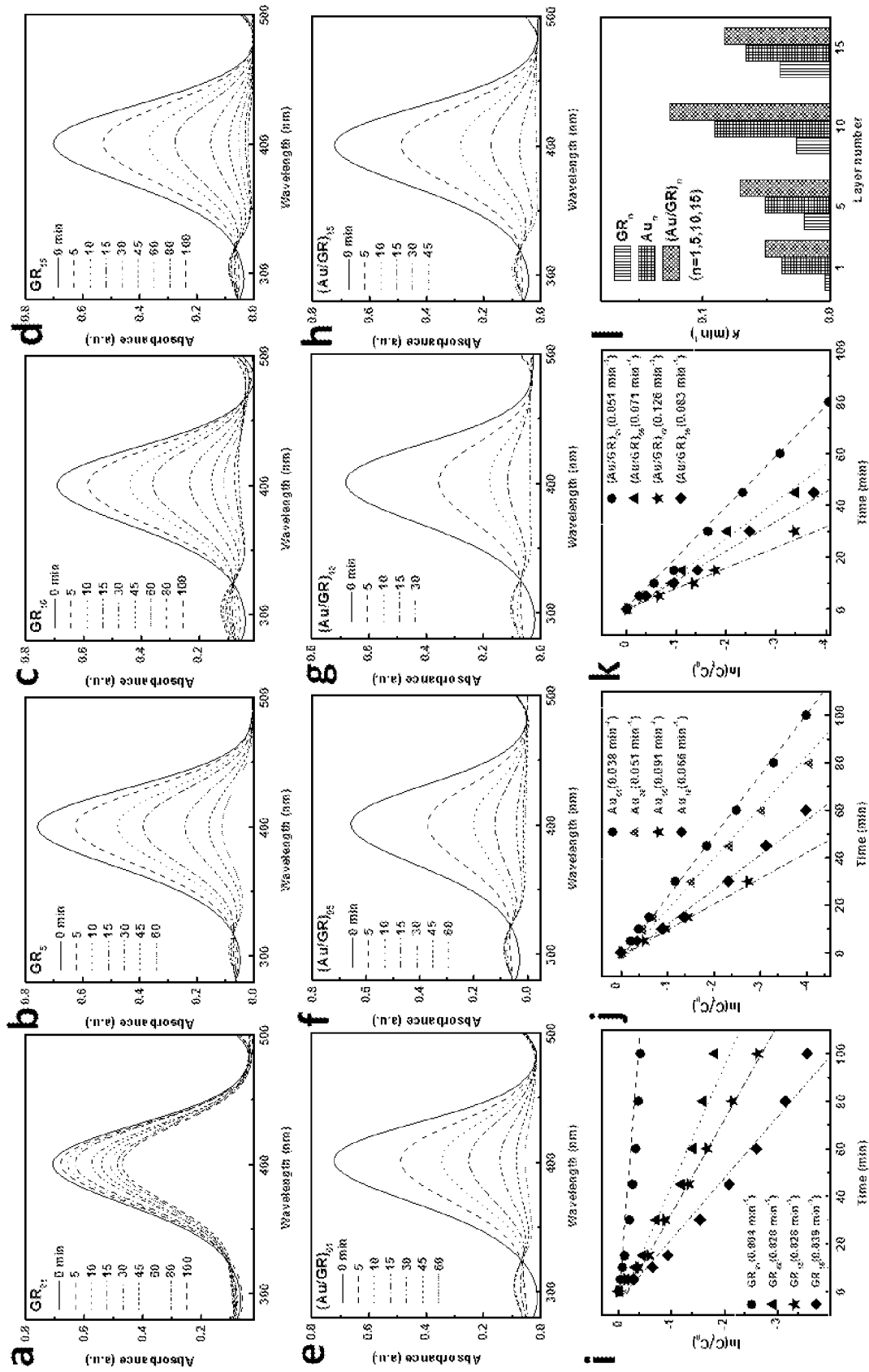

FIG. 17. Time-dependent UV/vis absorption spectra for the reduction of 4-nitrophenol over (a-d) GO$_n$ (n=1, 5, 10, 15) thin films catalysts, (e-h) (Au/GO)$_n$ (n=1, 5, 10, 15) hybrid thin films catalysts. (i-k) Plot of In(C$_t$/C$_0$) versus time for the reduction of 4-nitrophenol over different catalysts with an excess amount of NaBH$_4$ in aqueous media at ambient temperature by monitoring the decrease in the absorption intensity of 4-nitrophenol for the peak at 400 nm. (l) Comparison of reaction rate constants of GO$_n$, Au$_n$, and (Au/GO)$_n$ (n=1, 5, 10, 15) thin film catalysts.

Figure 18:
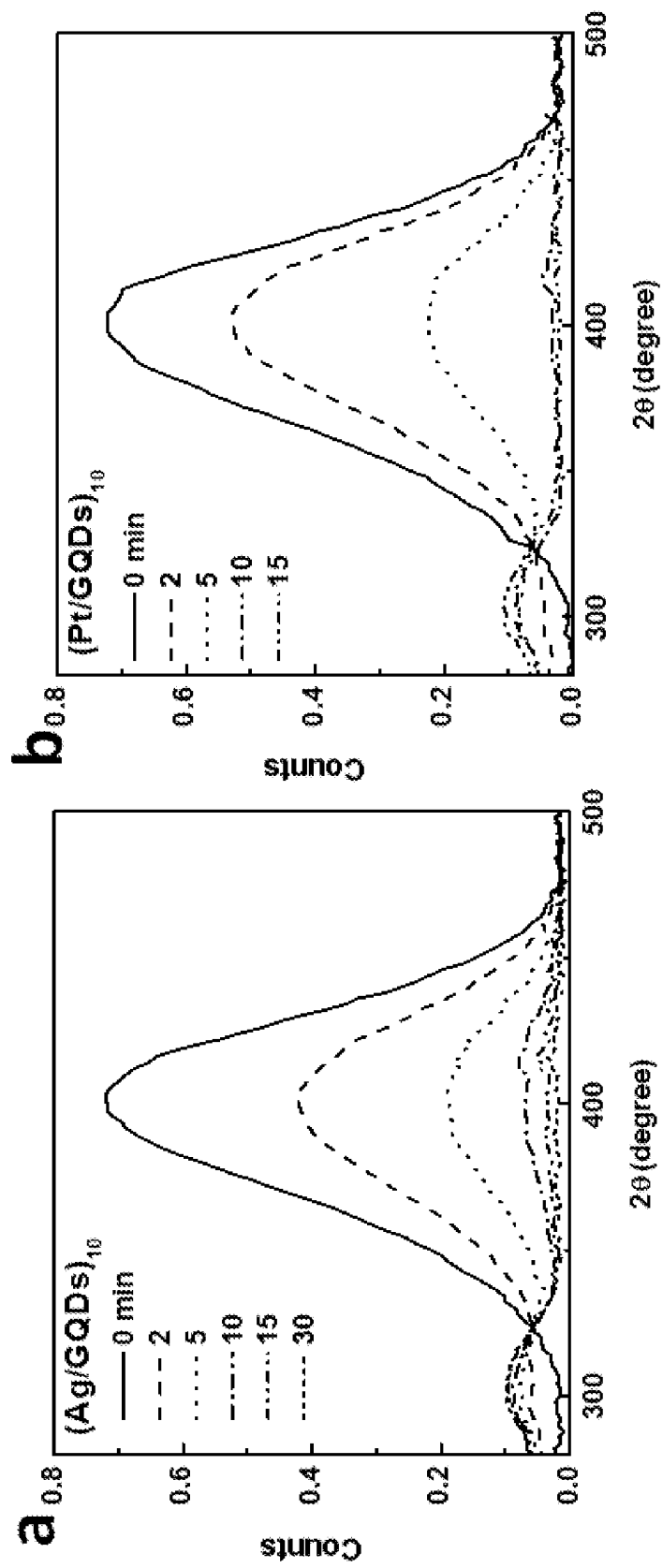

FIG. 18. Time-dependent UV/vis absorption spectra for the reduction of 4-nitrophenol over (a) (Ag/GQDs)$_{10}$, and (b) (Pt/GQDs)$_{10}$.

Figure 19:
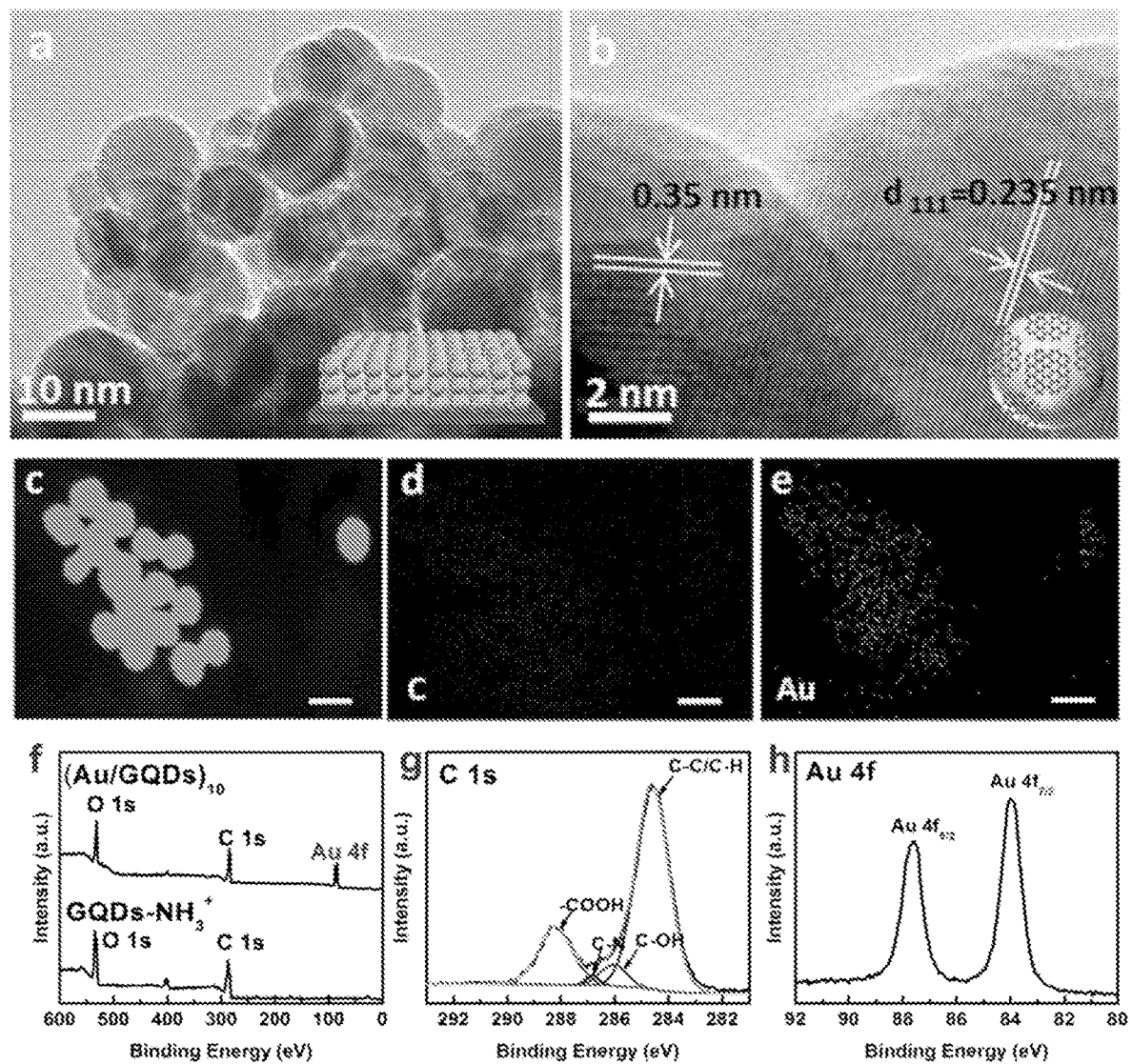

FIG. 19. TEM and HRTEM images of (a & b) (Au/GQDs)$_{10}$, (c) dark field-STEM image with corresponding elemental mapping results of (d) C and (e) Au (the scale bar is 20 nm), and (f) survey XPS spectra of (Au/GQDs)$_{10}$ film and GQDs-NH$_3^+$ in combination with high-resolution spectra of (g) C 1s and (h) Au 4f for (Au/GQDs)$_{10}$ film.

Figure 20:
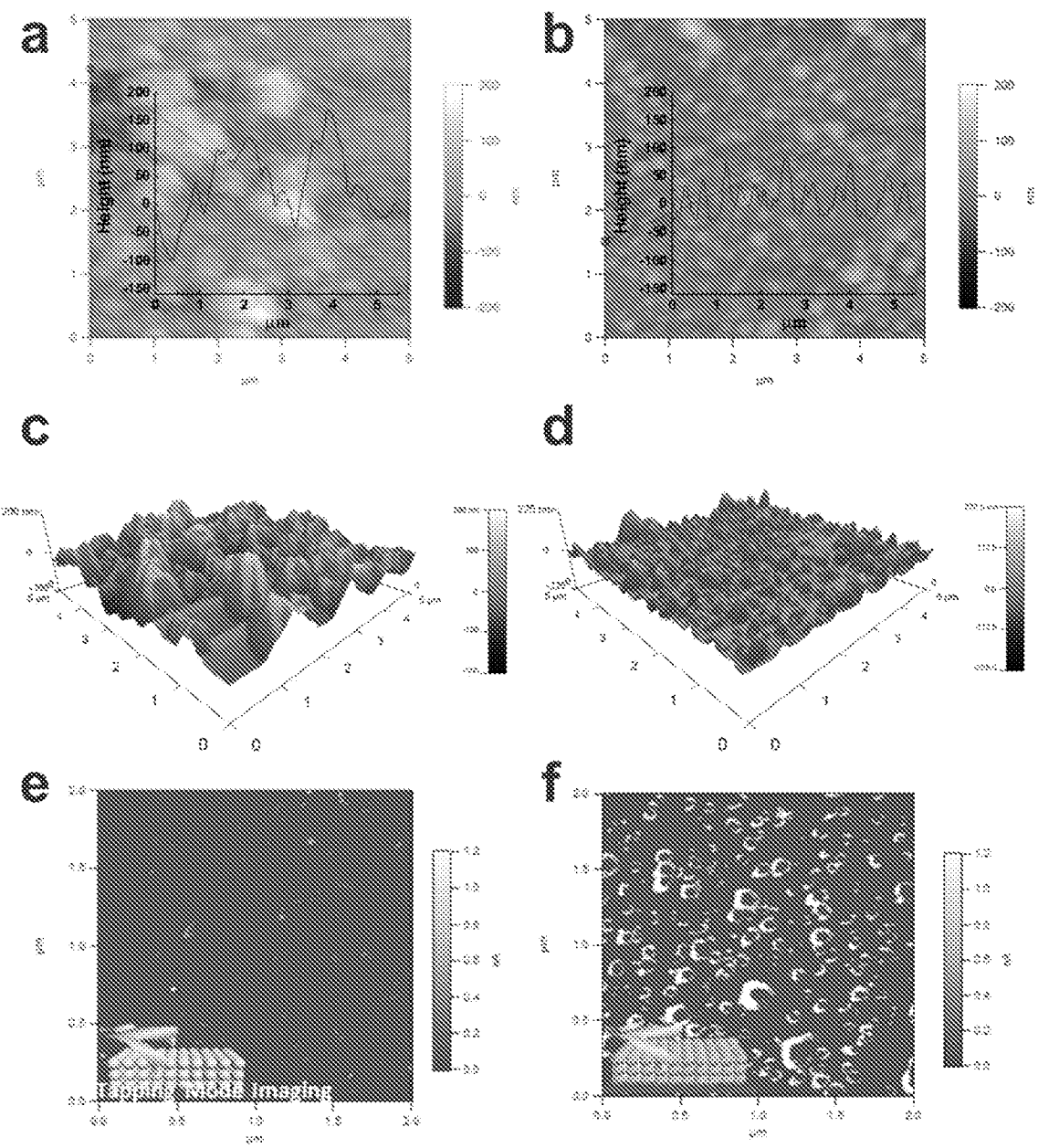

FIG. 20. AFM images of (a) (Au)$_{10}$ and (b) (Au/GQDs)$_{10}$ multilayer films with corresponding height profiles (inset) and 3D images in c and d, respectively. C-AFM dark current images of (e) (Au)$_{10}$ and (f) (Au/GQDs)$_{10}$ with a scan size of 2×2 μm and 10 mV bias potential was applied to the FTO substrate. The images provided in the insets depict the tapping modes for c-AFM measurements.

Figure 21:
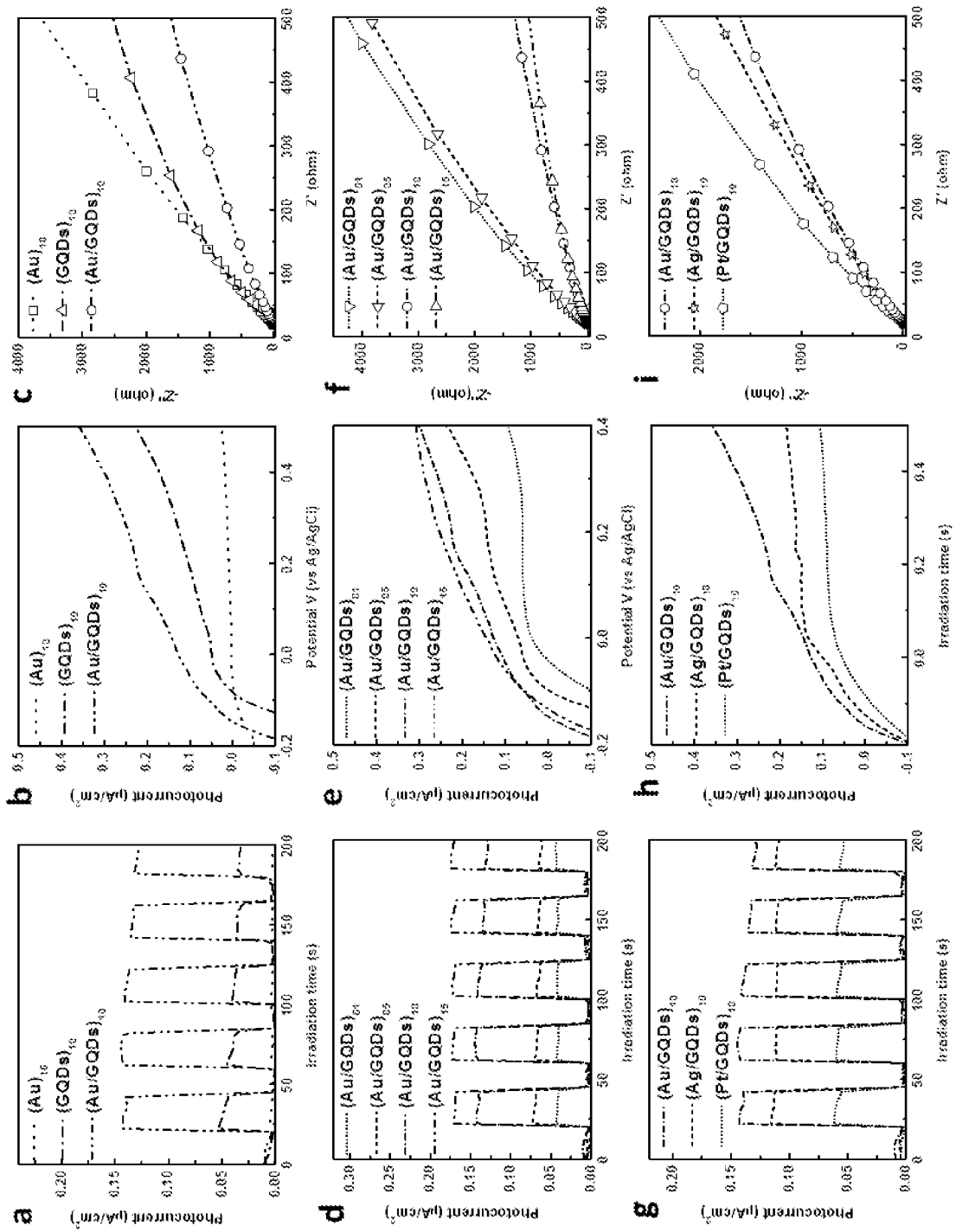

FIG. 21. (a, d, g) On-off transient photocurrent responses, (b, e, h) linear-sweep voltammograms (LSV, scan rate: 1 mV/s), and (c, f, i) electrochemical impedance spectroscopy (EIS) Nyquist plots in low-frequency region of (Au)$_{10}$ & (GQDs)$_{10}$ & (Au/GQDs)$_{10}$, (Au/GQDs)$_n$ (n=1, 5, 10, 15) and (M/GQDs)$_{10}$ (M=Au, Ag, Pt) multilayer thin films, respectively.

Figure 22:
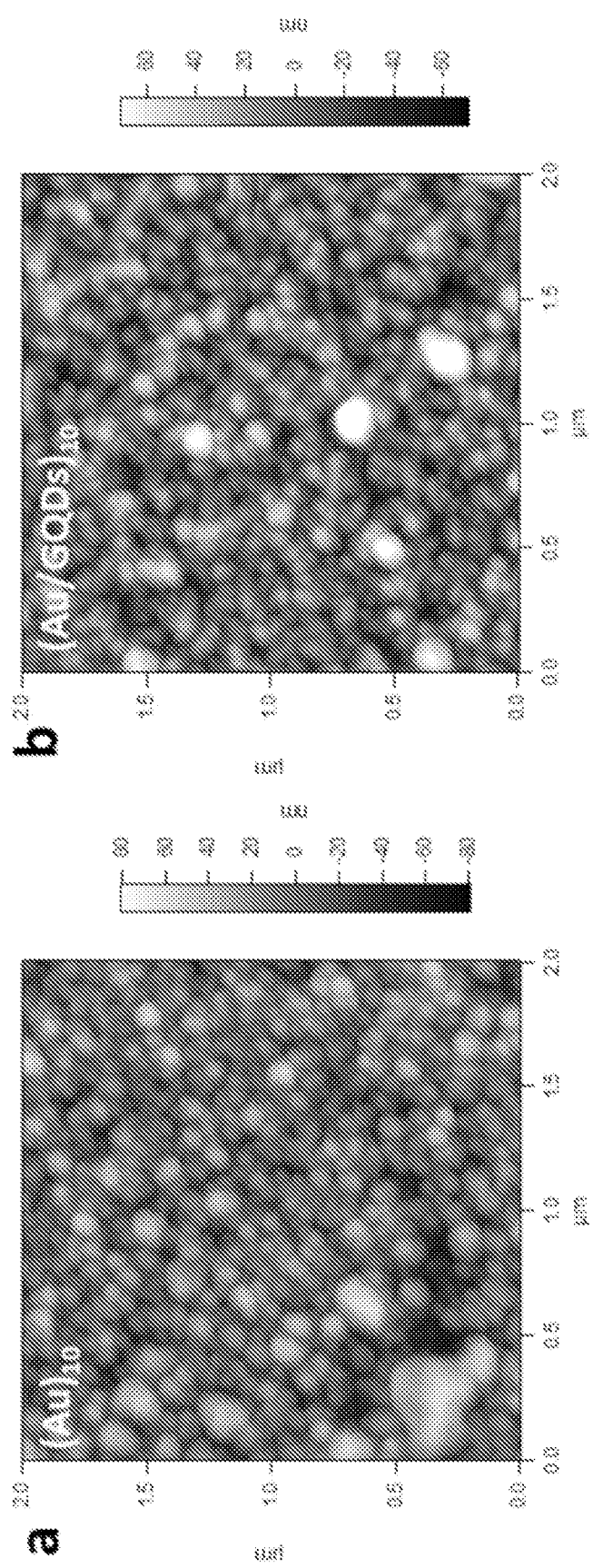

FIG. 22. c-AFM images of (a) (Au)$_{10}$ and (b) (Au/GQDs)$_{10}$ electrodes with a scan size of 2×2 μm and a 10 mV bias potential was applied to the FTO substrate.

Figure 23:
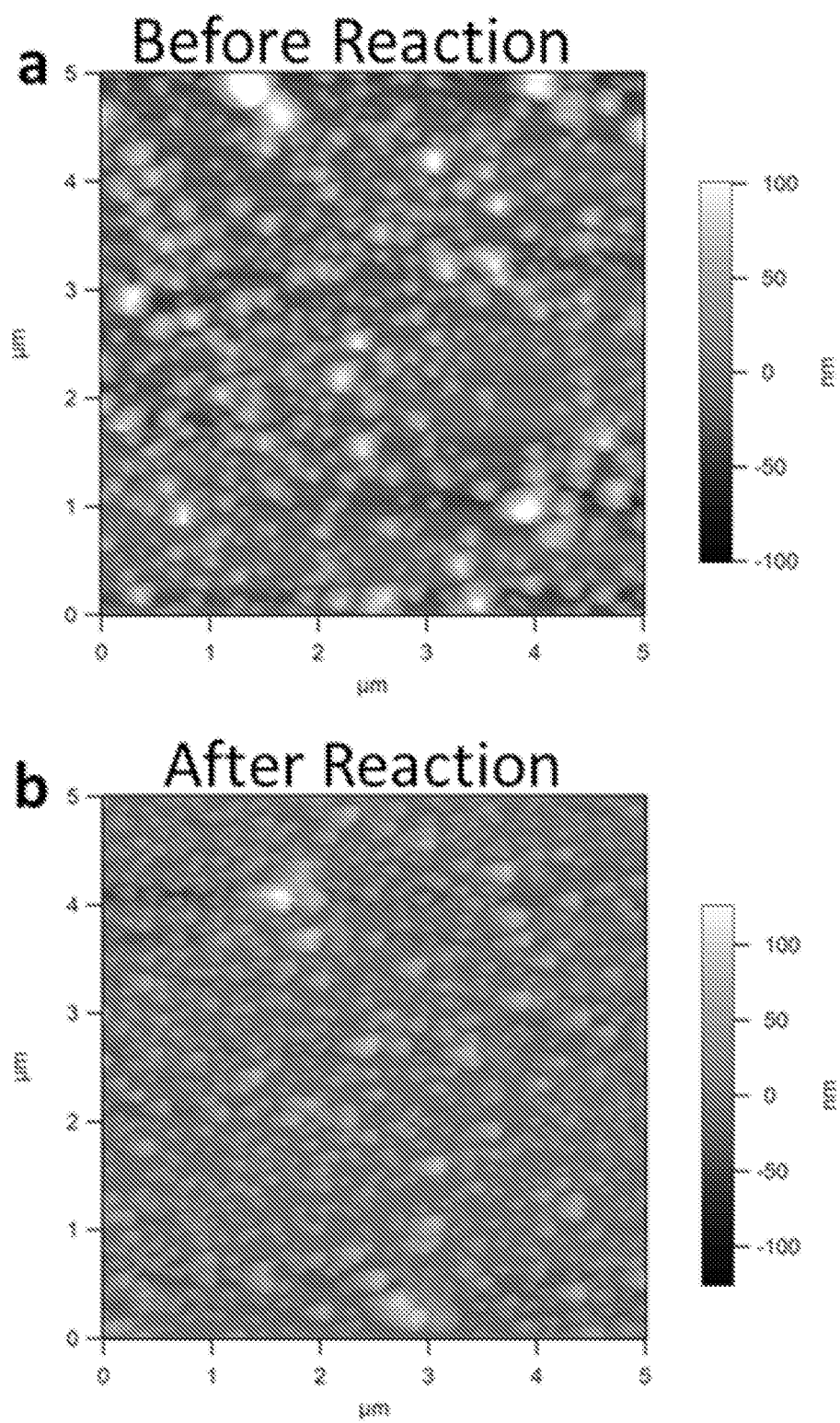

FIG. 23. AFM images of (Au/GQDs)$_{10}$ multilayer film before (a) and after (b) catalytic reduction reactions.

Figure 24:
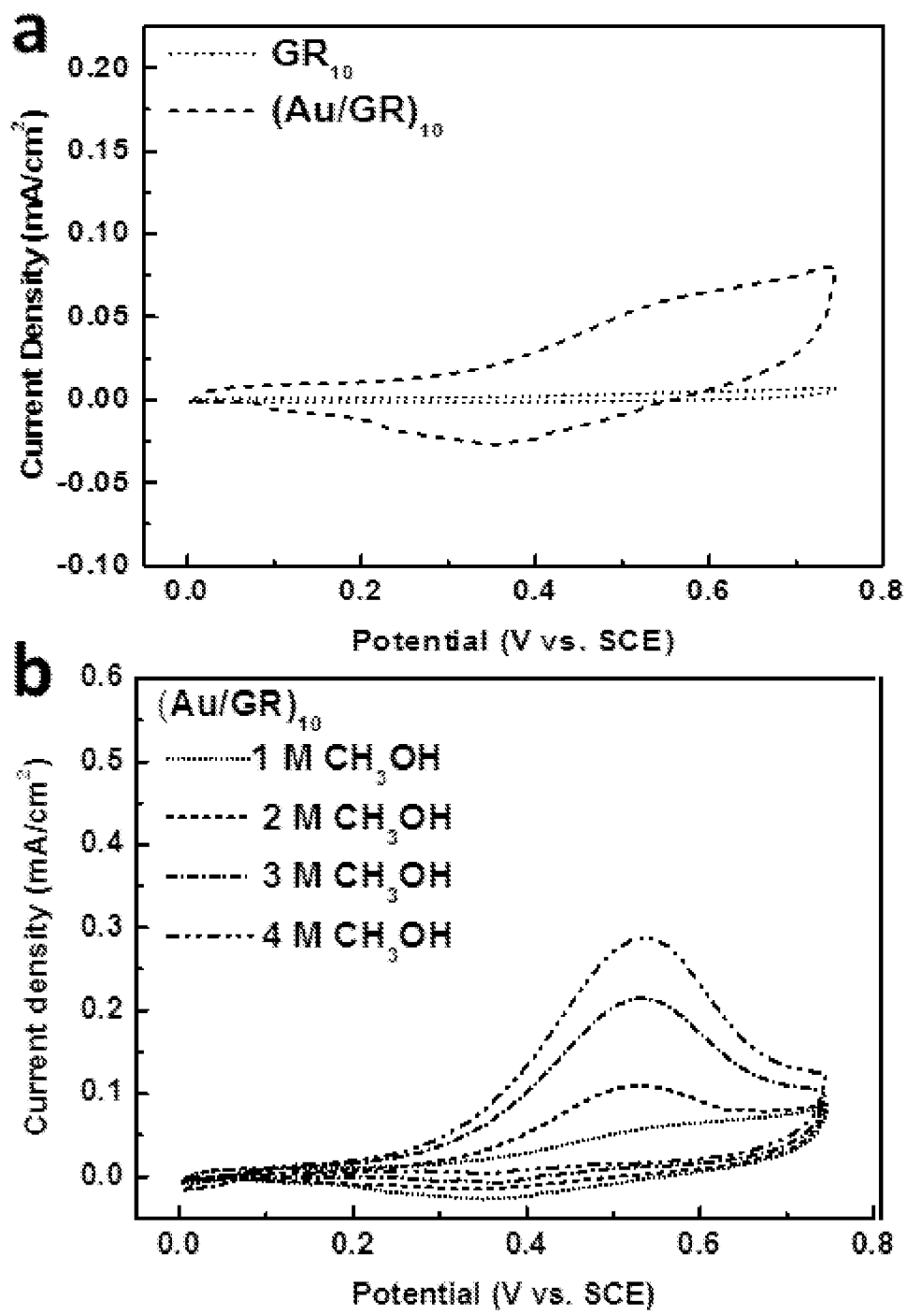

FIG. 24. (a) CV results of (GR)$_{10}$ and (Au/GR)$_{10}$ multilayer films measured in 0.10 M KOH with 1.0 M methanol in a saturated N$_2$ atmosphere under ambient conditions, and (b) CV results of (Au/GR)$_{10}$ multilayer thin film with different methanol concentration.

Figure 25:
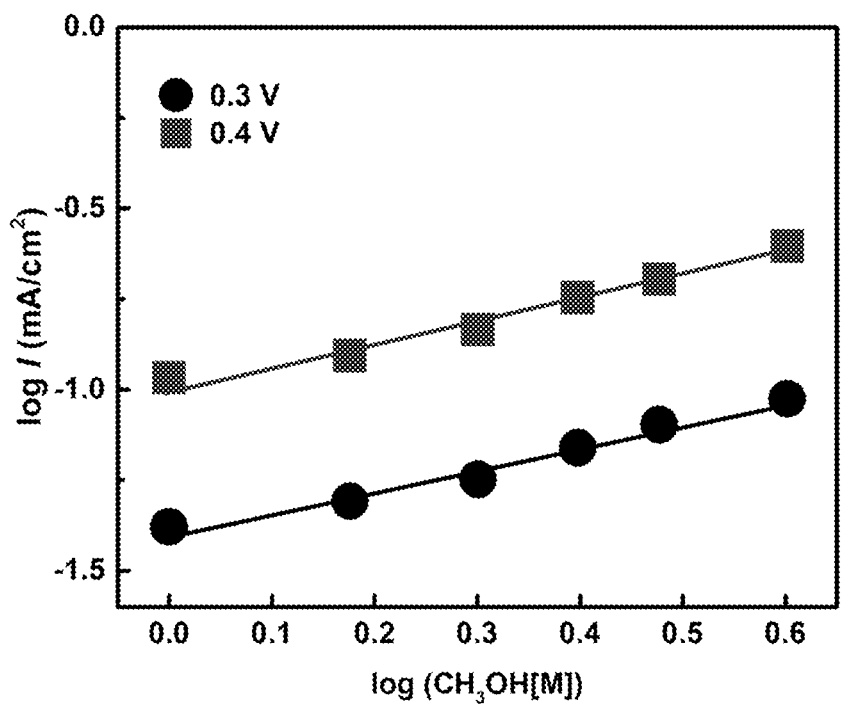

FIG. 25. Plots of log(l) against log(CCH$_3$OH) at different potentials in Tafel range.

Figure 26:
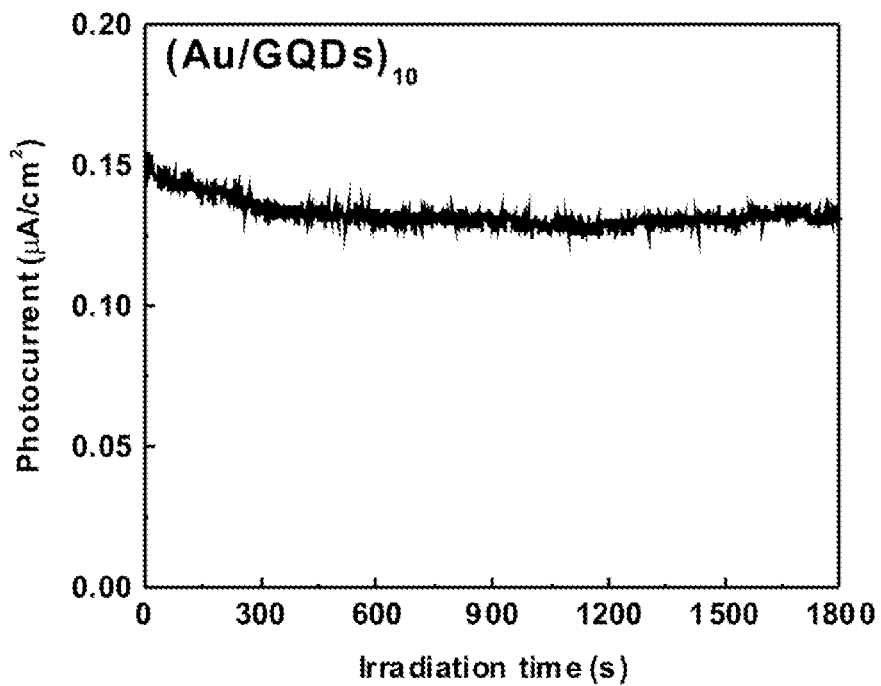

FIG. 26. Photocurrent of (Au/GQDs)$_{10}$ multilayer film under continuous simulated solar light irradiation.

Figure 27:
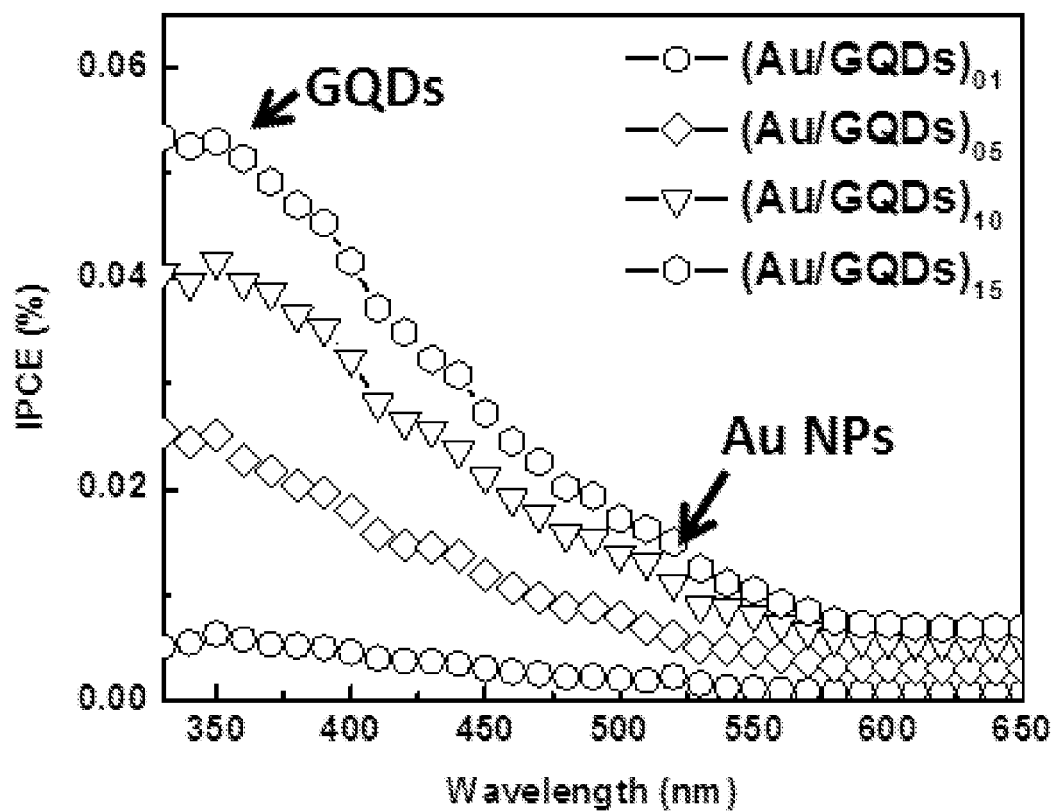

FIG. 27. IPCE spectra of (Au/GQDs)$_n$ (n=1, 5, 10, 15) multilayer thin films.

DESCRIPTION

The current invention relates to a tunable catalytic system that comprises well-defined and easy-to-fabricate M/GQDs (0D/0D) hybrid nanostructures, which can be manufactured in a more environmentally friendly manner. These materials show a wide variety of catalytic activities and also, catalytic stability. Thus, there is provided a multilayered composite thin film material comprising:
   a substrate having a positively-charged surface;
   a first bilayer material comprising:
      a layer of metal nanocrystal particles, each particle having a negatively charged surface, where the metal is selected from the group consisting of Ru, Rh, Os, Ir, Pd, Au, Ag and Pt, and the particles are attached to the substrate surface by charge attraction; and
      a coating layer of graphene quantum dots, each graphene quantum dot having a positively charged surface and attached to the layer of metal nanocrystal particles by charge attraction; and
   a 0 to $n^{th}$ additional bilayers comprising:
      a layer of metal nanocrystal particles, each particle having a negatively charged surface, where the metal is selected from the group consisting of Ru, Rh, Os, Ir, Pd, Au, Ag and Pt, and the particles are attached to the preceding layer of graphene quantum dots by charge attraction; and
      a coating layer of graphene quantum dots, each graphene quantum dot having a positively charged surface and attached to the layer of metal nanocrystal particles by charge attraction, where
      n is from 1 to 49.

In embodiments herein, the word "comprising" may be interpreted as requiring the features mentioned, but not limiting the presence of other features. Alternatively, the word "comprising" may also relate to the situation where only the components/features listed are intended to be present (e.g. the word "comprising" may be replaced by the phrases "consists of" or "consists essentially of"). It is explicitly contemplated that both the broader and narrower interpretations can be applied to all aspects and embodiments of the present invention. In other words, the word "comprising" and synonyms thereof may be replaced by the phrase "consisting of" or the phrase "consists essentially of" or synonyms thereof and vice versa.

As will be appreciated from the above, the term "multilayer" may refer to a composite material comprising the substrate, and one layer each of metal nanocrystals and graphene quantum dots (GQDs), which may be referred to herein as a "bilayer". However, the composite material may also comprise additional bilayers of metal nanocrystals and GQDs and so the composite material may have from 1 (n=0) to 50 (n=49) bilayers in total. For example, the composite material may have from 2 (n=1) to 20 (n=19) bilayers, such as from 5 (n=4) to 15 (n=14) bilayers, or, more particularly, 10 bilayers (n=9).

It is specifically intended that each layer of metal nanocrystals may be independently selected from the group consisting of Ru, Rh, Os, Ir, Pd, Au, Ag and Pt. As will be appreciated, this allows for each layer of metal nanocrystals in a composite material described herein to be different from the others, though any suitable combination may be used herein (e.g. all of the layers of metal nanocrystals in a composite material may use the same metal, or there may be alternating layers of two or more of the metals mentioned herein). All possible alternative arrangements of the metals used to form the metal nanocrystal layers in the composite materials disclosed herein are envisaged and form part of the current invention. Particular metals that may be mentioned herein include Pd, Au, Ag and Pt or, yet more particularly, Au, Ag and Pt.

As noted above, the bilayers are held together by charge attraction, wherein the GQDs have a positively charged surface, while the metal nanocrystals have a negatively charged surface. The positively charged surface of the graphene quantum dots may be provided by covalently bonded moieties comprising an ammonium ion functional group. Such groups may be provided by a suitable diamine moiety, such as ethylene diamine, which may be coupled with the surface of the graphene (or precursor graphene oxide—see below) using an amide coupling reagent, such as 1-[3-(dimethylamino)propyl]-3-ethylcarbodiimide methyliodide as discussed in more detail below. The negatively charged surface of the metal nanocrystals may be provided by moieties comprising carboxylate ions, such as by the use of a citrate salt (i.e. a salt of citric acid) to stabilize the metal nanocrystals.

The positively charged graphene quantum dots (GQDs-$NH_3^+$) used herein may have:
   (a) a particle size of from 3 to 20 nm, such as from 4 to 10 nm, such as 5.6 nm, optionally wherein the particles have a uniform size of from 3 to 20 nm, such as from 4 to 10 nm, such as 5.6 nm; and/or
   (b) a thickness of from about 0.7 to about 1.2 nm, or a thickness of from 1 to 2 layers of graphene; and/or
   (c) a measured zeta potential of from +40 mV to +70 mV, such as +53.5 mV when measured using a pH profile of from pH 7 to 12.

The metal nanocrystals may have:
   (a) an average diameter of from 3 nm to 20 nm, such as from 3.09 to 15 nm; and/or
   (b) a measured zeta potential of from −30 mV to −60 mV when measured using a pH profile of from pH 6 to 12.

Particular metal nanocrystals that may be mentioned herein include, but are not limited to: gold nanocrystals having an average particle size of from 12 to 17 nm (such as from 12.1 to 16.3 nm, such as 14.2 nm); silver nanocrystals having an average particle size of from 5 to 8 nm (such as from 5.77 to 7.17 nm, such as 6.47 nm); and platinum nanocrystals having an average particle size of from 2 to 4 nm (such as from 2.49 to 3.69 nm, such as 3.09 nm).

The composite materials may be electrically conductive. As such, the composite materials may display an image-average current of from 20 to 500 pA, such as from 50 to 250 pA, such as from 100 to 180 pA as measured by conductive atomic force microscopy. Without wishing to be bound by theory, this electrical conductivity may contribute to the good catalytic properties displayed by the composite materials disclosed herein.

A particular composite material that may be described herein is one in which, the metal nanocrystals (in all layers) are citrate-stabilized gold nanocrystals, n is 9 and the composite material has an image-average current of from 150 to 200 pA, such as 171.3 pA as measured by conductive atomic force microscopy.

In order to grow the multilayer structure described herein, it is required that a substrate is provided. In keeping with the negative surface charge of the nanocrystals, the substrate is required to have a positively charged surface in order to provide an attractive force that may conveniently assist in the self-assembly of the composite materials described herein. Suitable substrate materials may be selected from one or more of the group consisting of fluorine-doped tin oxide, glass, silicon, indium tin oxide (ITO), and titanium. It will be appreciated that the surface of these substrate materials may be provided with a coating of a polycationic polymer to provide the required positively charged surface. Any suitable polycationic polymer may be used. Suitable polycationic polymers include, but are not limited to poly-ethylenimine, poly(diallyldimethylammonium chloride) (PDDA), copolymers thereof, and blends thereof.

As noted above, the layered composite materials described herein are held together through charge attraction and may be formed by self-assembly. As such, it is noted that formation of such materials by self-assembly may be aided by having two materials that will exhibit a strong charge-attraction. This may be achieved, for example, where one of the materials displays a zeta potential that is at least +30 mV, while the other material displays a zeta potential that is at least −30 mV. Thus, the composite materials described above may be conveniently formed by a method of assembly that comprises the steps of:

(a) providing a substrate having a positively charged surface;
(b) dipping the substrate into a first solution comprising negatively charged metal nanocrystals, subsequently washing and drying the dipped material to form a negatively charged surface of metal nanocrystals;
(c) dipping the product of step (b) into a second solution comprising positively charged graphene oxide quantum dots, subsequently washing and drying the dipped material to form a positively charged surface;
(d) optionally repeating steps (b) and (c) n times using the product of step (c) as the substrate;
(e) subjecting the product of step (c) or, when conducted, step (d) to an annealing step under heat and an inert atmosphere, wherein:
n is from 1 to 49; and
the metal nanocrystals used in each step (b) are independently selected from the group consisting of Ru, Rh, Os, Ir, Pd, Au, Ag and Pt.

It will be appreciated that the preferences described above for the composite materials may also apply to the method described herein.

LbL as used herein demonstrates a number of advantages over conventional synthetic approaches in terms of its simplicity, accessibility, and versatility, which significantly furnishes ideal tunable control over micro-structure, thickness, and composition of the assemblies. Particularly, stable colloidal aqueous solutions including intrinsic negatively charged metal NCs and surface-modified positively charged GQDs render them suitable building blocks for LbL assembly buildup based on the pronounced electrostatic interaction, resulting in multilayer nanoarchitectures.

In the method above, graphene oxide quantum dots are used. The use of graphene oxide quantum dots may enable the formation of a more highly positively charged surface than otherwise possible if graphene quantum dots (obtained by reducing graphene oxide quantum dots) were used instead. This higher positive charge may be because there are more oxygen groups available to form covalent bonds with ammonium ion-containing moieties (e.g. ethylene diamine, where one of the amine groups forms a covalent amide bond with a suitable oxygen-containing moiety on the surface of the graphene oxide, with the other amine group being presented in its ammonium ion form) when a graphene oxide quantum dot is used, as compared to a graphene quantum dot (e.g. provided by the prior reduction of a graphene oxide quantum dot before reaction).

In the method above, a substrate having positively charged surface, which may be obtained as described hereinbefore, may be dipped into a first solution comprising negatively charged metal nanocrystals, which may be selected from those described hereinbefore, to form a negatively charged layer of metal nanocrystals. After suitable manipulations (e.g. washing and drying), the negatively charged layer of metal nanocrystals may be coated with a positively charged layer of graphene oxide quantum dots, which may in turn be coated with metal nanocrystals after it has been rinsed and dried. These processes involving the nanocrystals and quantum dots may be repeated until the final layer of graphene oxide quantum dots are laid, at which stage the intermediate composite material may be subjected to calcination under an inert atmosphere. The inert atmosphere may be nitrogen or a noble gas, for example argon. This calcination step serves to reduce the graphene oxide quantum dots to graphene quantum dots, while retaining the covalently-bound ammonium ions, thereby maintaining the structural integrity of the multilayer composite material and forming the final product, which comprises graphene quantum dots (i.e. reduced graphene oxide quantum dots).

The above method is a simple, green and easily accessible LbL assembly strategy to construct a series of well-defined M/GQDs (M=Ru, Rh, Os, Ir, Pd, or more particularly, Au, Ag, and Pt) multilayer composite thin film materials by taking full advantage of surface charge properties of metal NCs and graphene oxide quantum dots (GOQDs), in which negatively charged metal NCs and modified positively charged GOQDs are alternately deposited in a "face-to-face" integration fashion under substantial electrostatic attractive interaction. It will be appreciated that the use of the LbL method enables each layer of metal nanocrystals deposited to be different from the other layers, if so desired.

The resultant M/GQDs multilayer composite thin films have demonstrated versatile and highly efficient catalytic performance including selective reduction of aromatic nitro compounds in water and electrocatalytic oxidation of methanol at ambient conditions. The catalytic and electrocatalytic performances of these M/GQDs multilayer films can be easily tuned by assembly cycle and type of metal NCs. As such, the composite materials described herein may have a number of applications and the catalytic efficiency/performance may be tuned by controlling the number of GQD and metal NC bilayers in the catalyst for the particular application in question.

One of these applications where the materials may show particular promise is as a catalyst for organic reactions, due to the catalytic activity and surprising recyclability of the materials disclosed herein. Thus, there is also provided a method of catalysing an organic reaction comprising contacting one or more reagents for the organic reaction with a composite material as described herein and providing the conditions necessary to effect the organic reaction. The composite materials may be used to catalyse any suitable chemical reaction. For example, the composite materials (e.g. (Au/GQDs) having from 5 to 15 bilayers) may be useful in the catalytic reduction of aromatic nitro compounds to aromatic amine compounds in the presence of a suitable reducing agent (e.g. sodium borohydride).

A further organic chemical reaction that may be catalysed by the composite materials herein (e.g. (Au/GQDs) having from 5 to 15 bilayers) is the oxidation of methanol in an electrocatalytic reaction to produce carbon dioxide and energy. In a particular arrangement of this method, the method may involve placing a working electrode comprising a composite material described herein into an electrolyte solution containing methanol under an inert atmosphere. This is in essence a direct methanol fuel cell (DMFC).

DMFCs rely upon the oxidation of methanol on a catalyst layer on an anode to form carbon dioxide. Water is consumed at the anode that comprises the desired catalyst and is produced at the cathode. Protons are transported across a proton exchange membrane—often made from Nafion—to the cathode where they react with oxygen to produce water. Electrons are transported through an external circuit from anode to cathode, providing power to connected devices. Thus, the composite materials described herein may be used to form anodes for and thus form part of DMFCs.

The composite materials described herein may also be useful in methods for photodetection and/or energy harvesting (e.g. from light). As such, there is also provided a device for photodetection and/or energy harvesting comprising a composite material as described herein. The composite material may be provided as part of an electrode in such a device.

Finally, there is a method of energy (light) harvesting, which involves the steps of:
 (a) providing a light-transparent device comprising a working electrode comprising a composite material described herein, at least one other electrode as a counter electrode and an electrolyte;
 (b) irradiating the device with light to generate a photocurrent; and
 (c) converting water to hydrogen and oxygen.

Without wishing to be bound by theory, the catalytic properties of the composite materials disclosed herein may result from multiple cooperative synergies between zero-dimensional GQDs and metal NCs in the 3D LbL construct. These synergies may be manifested through enhanced functional performance and superior structural stability in selective catalytic, electrocatalytic and PEC reactions. The three catalytic mechanisms involving $(M/GQDs)_n$ multilayer thin films are discussed below. For selective catalytic reduction of aromatic nitro compounds, the predominant reason accounting for the remarkably enhanced catalytic activities of $(M/GQDs)_n$ multilayer thin films can be ascribed to the multifarious roles of GQDs. More specifically, intimately enwrapping metal NCs with GQDs afforded by LbL assembly can prevent the agglomeration of metal NCs, allowing exposure of more active sites on the surface, facilitating the adsorption of aromatic nitro compounds on the metal NCs surfaces owing to the analogous conjugate structure of GQDs framework to reactants, and boosting the stability of metal NCs. In particular, it should be emphasized that unique electronic structure of the zigzag edges on GQDs can interact with the terminal oxygen atoms of aromatic nitro compounds (Y. Choi et al., J. Mater. Chem. 21 (2011) 15431-15436), thus effectively weakening the N—O bonds for triggering the reduction reactions. In this regard, electrons in the reaction systems can be rapidly transferred from $BH_4$ to metal NCs with the assistance of GQDs which serves as an efficient interfacial electron relay medium, finally successfully achieving the reduction of aromatic nitro compounds at ambient conditions. As for the electrocatalytic methanol oxidation mechanism, two main factors influencing the highly efficient methanol oxidation performances of $(M/GQDs)_n$ multilayer thin films can be attributed to the methanol diffusion and mass transfer in conjunction with electron transfer in the LbL assembled thin films by the following pathways, which concurrently dictate the fine balance of $(M/GQDs)_n$ multilayer thin films electrodes during the electrocatalytic process.

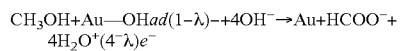

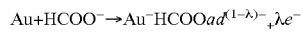

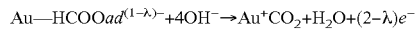

With regard to the PEC water splitting mechanism of $(M/GQDs)_n$ multilayer thin films, according to the Kohn-Sham molecular orbital (MOs) theory, various electron transitions from the occupied levels to the unoccupied levels can be triggered over GQDs under light irradiation, thereby imparting GQDs with a distinct Highest Occupied Molecular Orbital (HOMO)-Lowest Unoccupied Molecular Orbital (LUMO) gap which acts like a semiconductor with a small band gap (2.4-2.6 eV). [S. Yan et al., J. Phys. Chem. C. 115 (2011) 6986-6993; S. H. Jin et al., ACS Nano 7 (2013) 1239-1245] Accordingly, upon simulated solar light irradiation, electrons are photoexcited from the HOMO to the LUMO of GQDs to generate electron-hole pairs. Subsequently, photoinduced electrons could be partly captured by metal NCs which serve as efficacious electron traps resulting in efficient separation of photogenerated electron-hole pairs over GQDs. On the other hand, it should be stressed that hot electrons formed in-situ from the photo-induced SPR excitation on Au NCs might be simultaneously produced and then flow to the LUMO of GQDs, which increases the photoelectrons density of the whole reaction system. Thus, hot electrons and bandgap photoexcited electrons rapidly flow to the counter electrode to reduce water to hydrogen. Meanwhile, photogenerated holes produced on the HOMO of GQDs and, hot holes on Au NCs oxidize water to oxygen, thereby achieving the successful separation of electron-hole charge carriers and producing the photocurrent.

The invention will now be further described with reference to the following non-limiting examples.

EXAMPLES

Characterizations

Scanning electron microscopy (SEM) images were acquired with field emission scanning electron microscopy (JEOL, JSM-6700F). Transmission electron microscopy (TEM) and high-resolution transmission electron microscopy (HRTEM) images were achieved by using a JEOL model JEM2010 EX instrument at an accelerating voltage of 200 kV. X-ray photo electron spectroscopy (XPS) measurements were collected through ESCALAB 250 photoelectron spectrometer (Thermo Fisher Scientific) at $2.4 \times 10^{-10}$ mbar. Binding energy (BE) of the element was calibrated to the BE of carbon (284.60 eV). Atomic force microscopy (AFM) images were obtained by using MFP3D microscope, Asylum Research. UV-vis spectra were recorded on a Shimadzu UV2501 spectrophotometer in which $BaSO_4$ was used a background ranging from 300 to 800 nm. The fluorescence spectra were collected by a Fluoromax-4, Horiba Jobin Yvon Spectrofluorometer with a photon-counting detection system to detect fluorescence emission. Sample excitation was obtained by using a diode laser, BWF-2 (980 nm, $P_{max}$=1.0 W at 3.0 A, B&W TEK Inc.) with an optical fiber (100 μm core). Fourier Transform Infrared Spectroscopy (FTIR) was conducted in a Digilab FTS 3100 instrument by collecting 45 scans with a resolution of 4 $cm^{-1}$. The crystal phase of the samples was recorded by X-ray diffraction (XRD, Bruker D8 Advance X-ray diffractometer) with Cu Kα radiation. The zeta potential of samples was measured by dynamic light scattering analysis (Zeta PALS, Brookhaven Instruments Co.). Raman results were collected by using Raman spectroscopy (Renishaw) equipped with a 633 nm laser source.

Preparation of Graphene Oxide Quantum Dots (GQDs) and Graphene Oxide

Graphene oxide quantum dots (GOQDs) were prepared with CX-72 carbon black via being refluxed in a concentrated nitric acid ($HNO_3$) solution (Choi, Y et al., Adv Energy Mater 2012, 2, 1510-1518; Zeng, Z. et al., Sci Rep-Uk 2016, 6). Typically, 0.4 g dried CX-72 carbon black was added to 6 mol L$^{-1}$ nitric acid (100 mL) and refluxed for 24 h at 110° C. After cooling to below 30° C., the product was centrifuged (12000 rpm) for 10 min to achieve a sediment and a supernatant. The resultant supernatant was treated at 200° C. to evaporate the nitric acid and water. After cooling to room temperature, a reddish-brown solid was acquired. Finally, the GOQDs aqueous solution were obtained by dissolving the GOQDs in deionised H$_2$O, followed by 10 minutes of sonication.

Positively charged GOQDs (GOQDs-NH$_3^+$) were prepared via the 1-[3-(dimethylamino)propyl]-3-ethylcarbodiimide methyliodide and ethylene diamine (EDC)-mediated amine exchange reaction (Hong, J. et al., Acs Nano 2012, 6, 81-88). As an example of the process, 0.5 g of 1-[3-(dimethylamino)propyl]-3-ethylcarbodiimide methyliodide were dissolved in 4 mL of ethylene diamine, and the mixture was added into 40 mL of the negatively charged GOQD solution (0.5 mg/mL) formed above. The mixed solution was rapidly stirred for 12 h, and then dialyzed for 3 days in a membrane tube (MWCO=12000-14000 Da) to remove any residual chemicals after the reactions.

Positively charged graphene oxide (GO-NH$_3$) was prepared via the 1-[3-(dimethylamino)propyl]-3-ethylcarbodiimide methyliodide and ethylene diamine (EDC)-mediated amine exchange reaction (Hong, J. et al., Acs Nano 2012, 6, 81-88). The process is similar to that described above for GOQDs.

Characterization of GOQDs-NH$_3^+$:

As displayed in FIG. 10, the TEM image shows a uniform size for the GOQDs-NH$_3^+$ (ca. 5.6 nm) and the lattice-fringe spacing in the high-resolution (HR) TEM image (inset, FIG. 10) was determined to be ca. 0.35 nm, corresponding well to the (002) crystal planes of graphite. The atomic force microscope (AFM) image shows that the height profile of the GOQDs-NH$_3^+$ obtained is around 0.7~1.2 nm, suggesting that the product obtained consists of 1-2 graphene layers. The physical properties of pristine GOQDs were retained after EDC modification. As shown in FIG. 11, the zeta potential of both GOQD-NH$_3^+$ and GO-NH$_3^+$ (preparation described above) aqueous solutions exhibited substantial positive values, for instance, +55.2±1.6 mV and +48.7 mV in a pH profile ranging from 7 to 12, respectively. It is well-established that a zeta potential greater than ±30 mV is the criterion that ensures the stability of a colloidal aqueous solution, due to sufficient electrostatic repulsion of the particles. Thus, stable surface charge properties of constituent ingredients for LbL assembly can be rationally tuned by altering the pH values of metal NCs and GOQD aqueous solutions used.

Synthesis of Negatively Charged Citrate-Stabilized Metal Nanocrystals

Citrate-stabilized gold nanocrystals (NCs) were prepared by the Dotzauer method (Dotzauer, D. M. et al., Nano Lett 2006, 6, 2268-2272). Briefly, all glassware was cleaned thoroughly with aqua regia (HCl/HNO$_3$=3:1) and rinsed with DI water. 50 mL of aqueous 1 mM HAuCl$_4$·3H$_2$O was heated to a rolling boil with stirring. 5 mL of 38.8 mM sodium citrate dihydrate was also heated to a rolling boil and then added rapidly to the gold solution. After 20 seconds, the mixture became dark and then burgundy, and was subsequently heated with stirring for 10 min and then stirred without heating for an additional 15 min.

Citrate-stabilized silver NCs were prepared according to Lee's approach (Yang, J. et al., J Phys Chem B 2005, 109, 19208-19212). Briefly, 100 mL of 1 mM aqueous AgNO$_3$ solution was mixed with 8 mL of a 40 mM aqueous sodium citrate solution used as stabilizer. 2 mL of a 112 mM aqueous NaBH$_4$ solution was then added dropwise under vigorous stirring at ambient temperature, immediately yielding a yellowish brown Ag hydrosol. The Ag hydrosol was subsequently placed in a refrigerator at 4° C. and aged for 24 h to decompose the residual NaBH$_4$ before it was used in subsequent steps.

Citrate-stabilized platinum NCs were prepared by Elliott's method. Specifically, 26 mL of 2.8 mM aqueous trisodium citrate dehydrate solution was added to 50 mL of 0.4 mM aqueous hydrogen hexachloro-platinate solution at room temperature. An amount of 5 mL of 12 mM NaBH$_4$ was then introduced dropwise with vigorous stirring, and the pale yellow solution turned dark brown in 5 min. Finally, the dark brown colloidal solution was stirred for 4 h and stored in a refrigerator at 4° C. for further use.

Characterization of Citrate-Stabilized Metal Nanocrystals:

As shown in the TEM images (FIG. 9), the metal NCs of Au, Ag, and Pt demonstrated average diameters of 14.2±2.1, 6.47±0.7, and 3.09±0.6 nm, respectively. Moreover, it is apparent from FIGS. 9 d-f that these colloidal metal NC aqueous solutions exhibit narrow size distributions and excellent monodispersivity, which is attributed to the substantial electrostatic repulsion between metal NCs. Selective area electron diffraction (SAED) patterns in the inset of FIGS. 9(a-c) (FIG. S1(a-c)) substantiate the polycrystalline nature of the metal NCs. Zeta potential results, as displayed in FIG. 11, show that all of these metal NCs have pronounced negatively charged surfaces over a wide pH profile (2-12), which favors spontaneous electrostatic assembly with positively-charged counterparts.

Example 1: LbL Assembly of (M/GQDs)$_n$ (M=Au, Ag, Pt NCs, n=1, 5, 10, 15) Multilayer Composite Thin Films FIG. 1 illustrates the flowchart for LbL assembly of (M/GQDs)$_n$ multilayer composite thin films. Intrinsically negatively charged metal NCs (10) and positively charged GOQDs (20) were utilized as the main building blocks for LbL assembly buildup (30). It should be emphasized that metal NCs surfaces were capped by a large amount of citrate ions which generally deprotonate in aqueous solution and thus afford the metal NCs a negatively charged surface. GOQDs were judiciously modified with the EDC molecule which converts the surface charge of GOQDs from negative to positive and are discussed herein as GOQDs-NH$_3^+$. The pronounced electrostatic attractive interaction between the negatively charged metal NCs and positively charged modified GOQDs provides a solid foundation for LbL assembly of various (M/GQDs)$_n$ multilayer composite films.

Method

Fluorine-doped tin oxide (FTO) or silicon wafer substrates were thoroughly cleaned in a freshly prepared "piranha" solution (3:1 concentrated 98% H$_2$SO$_4$/30% H$_2$O$_2$; Caution: piranha solution reacts violently with organic materials and should be handled with great care). Firstly, the substrate was dipped into polyethylenimine (PEI) aqueous solution (1.0 mg/mL, 0.5 M NaCl, pH=7.23) for 10 min and washed three times with DI H$_2$O, followed by drying with a gentle stream of N$_2$. Subsequently, the resultant substrate was immersed in around 3 mL of the as-prepared (see above) negatively charged metal aqueous solution for 10 min and then subjected to the same washing and drying treatments. Afterwards, the substrate was dipped into 3 mL of a surface charge modified GOQDs (or GO) aqueous suspension (1.0 mg/mL, pH=7.0) for 10 min, rinsed with DI H$_2$O, and dried by a stream of $N_2$, producing a $(M/GOQDs)_1$ (or a $(M/GO)_1$) multilayer thin film. The above procedure as a whole was designated as one assembly cycle. Multilayer $(M/GOQDs)_n$ (or $(M/GO)_n$) composite thin films with varied assembly cycles were prepared by alternate deposition of positively charged GOQDs (GO) and negatively charged metal NCs.

For comparison, pure $(GQDs)_n$, graphene layers $((GR)_n)$, (metal NCs)$_n$, multilayer thin films were prepared. For the preparation of pure $(GQDs)_n$ (or $(GR)_n$) multilayer thin films, the substrate was dipped into poly (sodium 4-styrenesulfonate) (PSS, 1.0 mg/mL, pH=7.0) aqueous solution for 10 min and washed three times with DI $H_2O$, followed by drying with a gentle stream of $N_2$. Subsequently, the resultant substrate was immersed in 3 mL of a surface charge modified GOQDs (or GO) aqueous solution for 10 min and then subjected to the same washing and drying treatments, producing $(GOQDs)_1$ (or $(GO)_1$) multilayer thin film. The above procedure as a whole was designated as one assembly cycle. Multilayer $(GOQDs)_n$ (or $(GO)_n$) thin films with varied assembly cycles were prepared by alternate deposition of negatively charged PSS and positively charged GOQDs (or GO).

Multilayer (metal NCs)$_n$ thin films with varied assembly cycles were prepared by alternate deposition of positively charged PEI and negatively charged as-prepared metal NCs.

Finally, the LbL-assembled multilayer composite films were calcined in an argon atmosphere, which involved heating the composites from 25° C. to 200° C. at a heating rate of 5° C./min. once a temperature of 200° C. was reached, it was maintained for 1 h. The above process resulted in the substantial reduction of the graphene oxide to graphene, thereby providing multilayer assemblies comprising graphene quantum dots (GQDs) and graphene layers (GR). That is, the resulting products after calcination in argon were multilayer $(M/GQDs)_n$ and $(M/GR)_n$ composite thin films.

Characterization

Transmission electron microscopy (TEM) was used to probe the microscopic structure of $(M/GQDs)_{10}$ multilayer composite films. As shown in FIGS. 2(a, c, e), Au, Ag, and Pt NCs, respectively, are uniformly distributed in the $(M/GQDs)_{10}$ multilayer composite films with intimate interfacial integration with GQDs, which can be unambiguously revealed by corresponding high-resolution TEM (HRTEM) images. As manifested in FIGS. 2(b, d, f), the lattice fringe of 0.35 nm can be indexed to the (002) crystal plane of GQDs and lattice spacings of 0.235, 0.232, and 0.241 nm are attributed to the (111) crystallographic plane of face-centered cubic (fcc) Au, Ag, and Pt NCs, respectively.

Field-emission scanning electron microscopy (FESEM) and atomic force microscopy (AFM) images were also utilized to probe the specific morphologies of different multilayer composite films. As displayed in FIG. 12, (Au/GQDs)$_n$ (n=1, 5, 10, 15) multilayer composite films exhibited relatively flat surface with Au NCs evenly deposited on it and density of Au NCs increases with increasing the assembly cycles (FIG. 13), implying the LbL assembly approach developed is efficient in fabricating (Au/GQDs)$_n$ multilayer films based on electrostatic attractive interaction between ingredients. This can be further corroborated by the successful fabrication of (Ag/GQDs)$_n$ and (Pt/GQDs)$_n$ multilayer films, as reflected by FIG. 14. For comparison, pure (Au)$_n$ and (Au/GO)$_n$ multilayer films were also fabricated via analogous LbL assembly route and their morphologies were displayed in FIG. 12 and FIG. 12, respectively. It is evident that (Au/GQDs)$_{10}$ multilayer film demonstrated a smoother surface with less agglomeration of NCs. On the contrary, serious agglomeration of Au NCs was observed in the (Au)$_n$ (n=1, 5, 10, 15) multilayer thin films (FIG. 12), probably due to the lack of a supporting substrate.

Elemental mapping results (FIG. 19c-e) confirmed the coexistence of C and Au signals in the (AU/GQDs)$_n$ multilayer thin film with a homogenous distribution.

X-ray photoelectron spectroscopy (XPS) is used to explore the composition and elemental chemical states of different $(M/GQDs)_n$ multilayer films. FIG. 3a shows the survey spectra of $(M/GQDs)_{10}$ (M=Au, Ag, Pt) multilayer composite films (FIG. 3), for which the characteristic of C 1s, N 1s, and O 1s signals originate from GQDs-$NH_3^+$, and Au 4f, Ag 3d, as well as Pt 4f signals arise from metal NCs, indicative of successful combination of metal NCs and GQDs-$NH_3^+$ in the composite films. Alternatively, to differentiate the elemental state and specific chemical bond species of the samples, high-resolution C 1s spectrum of $(M/GQDs)_{10}$ hybrid thin film (FIG. 3b) was deconvoluted to four peaks showing band energy of 284.60, 286.15, 286.85, and 288.20 eV, corresponding to C—C/C—H, C—OH, C—N, and COOH species from GQDs-$NH_3^+$. The featured Au $4f_{7/2}$ and Au $4f_{5/2}$ peaks with band energy of 84.05, and 87.75 eV (FIG. 3c) are consistent with that of metallic $Au^0$. Analogously, featured Ag $3d_{5/2}$ and Ag $3d_{3/2}$ in the Ag 3d spectrum present two peaks at 368.20 and 374.25 eV (FIG. 3d), and the band energy of 71.25 (Pt $4f_7/2$) and 74.70 eV (Pt $4f_{5/2}$) (FIG. 3e) should arise from metallic $Pt^0$. As a result, these high-resolution spectra of Au 4f, Ag 3d, and Pt 4f distinctly prove that the chemical and electrical state of metallic Au, Ag, and Pt were retained in the metal NCs when combined with GQDs-$NH_3^+$ via pronounced electrostatic force for the current LbL self-assembly approach.

Optical properties of $(M/GQDs)_n$ multilayer composite thin films were studied by UV-vis diffuse reflectance spectra (DRS). As mirrored in FIG. 4a, DRS results of (Au/GQDs)$_n$ multilayer films demonstrated two typical absorption peaks located at ca. 350 and 514 nm which are attributed to the characteristic peak of GQDs and surface plasmon resonance (SPR) peak of Au NCs, respectively. DRS results of (Ag/GQDs)$_{10}$ multilayer thin films (FIG. 4c) concurrently demonstrated two peaks at 355 and 410 nm, which are attributed to typical absorption peak of GQDs and SPR peaks of Ag NCs, respectively. No obvious absorption peak was observed in the DRS result of (Pt/GQDs)$_{10}$ multilayer thin film due to the absent absorption of Pt NCs in the visible region.

Absorption intensity of the two peaks for the (Au/GQDs)$_n$ films increases proportionally with assembly layer (FIG. 4b), strongly substantiating the gradual growth of (Au/GQDs)$_n$ multilayer films in which Au NCs and GQDs components were alternately integrated in a controllable mode via LbL assembly approach. Correspondingly, as shown in FIG. 4d and FIG. 4e, Raman spectra of (Au/GQDs)$_n$ (n=1, 5, 10, 15) multilayer films suggest that peak intensity of typical D and G bands arising from GQDs also increases proportionally with the assembly layer, thus once again verifying alternate intercalation of GQDs layers in the composite films.

Analogous D and G bands signals were also observed in the Raman results of (Ag/GQDs)$_{10}$ and (Pt/GQDs)$_{10}$ multilayer thin films (FIG. 4f) which were fabricated via the same LbL assembly approach. Thus, DRS and Raman results evidenced successful fabrication of multilayered $(M/GQDs)_n$ (M=Au, Ag, Pt) thin films.

The analogous DRS and Raman results were also observed in the (Au/GR)$_n$ counterpart multilayer films which were constructed by the same LbL assembly approach except for replacing 0D GQDs with 2D GR (FIG. 15). Thus, the results concurrently evidence the formation of multilayered nanostructures in (Au/GQDs)$_n$ and (Au/GR)$_n$ composite films and thus affirm the versatility of LbL assembly strategy, for example, in constructing different multilayer thin films regardless of the dimensionality of carbon materials. Furthermore, it should be noted that, distinct from the Raman result of (Au/GR)$_n$ counterpart films (FIG. 15), substantial peak broadening and bathochromic shift of D and G bands were observed in (Au/GQDs)$_n$ films with increasing the assembly layer, indicative of significantly enhanced interaction between Au NCs and GQDs in the intimately stacked 0D/0D (Au/GQDs)$_n$ films in comparison with the interaction between Au NCs and GR in 0D/2D (Au/GR)$_n$ films (Li, D. et al., Nat Nanotechnol 2008, 3, 101-105; Yuan, W. Y. et al., Langmuir 2009, 25, 7578-7585).

Conductive atomic force microscopy (c-AFM) was subsequently employed to probe the nanoscale electronic properties and size-dependent electron transport efficiency of hybrid multilayer films [Z. He et al., Adv. Mater. 25 (2013) 6900-6904]. In this imaging mode, a conductive tip scans over the film surface to collect charge carriers at a 10 mV applied bias in the dark (inset, FIG. 20) and the nanoscale current distribution of the samples were presented. The dark current (FIG. 20) of (Au)$_{10}$ and (Au/GQDs)$_{10}$ multilayer thin films depicted an image-average current (171.3 pA) for (Au/GQDs)$_{10}$, which is over 30 times higher than that of (Au)$_{10}$ (5.6 pA). The high average current of (Au/GQDs)$_{10}$ is indicated by the bright area (high-current) in the whole scanned area. The corresponding topography images from c-AFM measurements of (Au)$_{10}$ and (Au/GQDs)$_{10}$ multilayer thin films are given in FIG. 22. This observation implies the formation of a more continuous electron transport network in the (Au/GQDs)$_{10}$ multilayer film, leading to more efficient electron transport, and more surprisingly higher current density and enhanced catalytic performances as discussed below.

Example 2: Selective Catalytic Reduction of Aromatic Nitro Compounds

Chemical reduction of 4-nitrophenol (4-NP) to 4-aminophenol in aqueous media under ambient conditions was used as probe reaction to evaluate the catalytic performances of different multilayer composite films.

Method

As a representative example, the catalytic properties of (M/GQDs)$_n$ (M=Au, Ag, Pt; n=1, 5, 10, 15) multilayer thin films were evaluated by employing the reduction of aromatic nitro compounds to corresponding amino compounds by NaBH$_4$ as a model reaction. In a typical reaction, a (M/GQDs)$_n$ sample (20 mm×10 mm) with an area of 2 cm$^2$ was dipped into an aqueous solution in a quartz cuvette containing 2 mM (40 μL) of an aromatic nitro compound, 100 mM (400 μL) NaBH$_4$, and 2 mL DI H$_2$O. Afterwards, the mixture was stirred at room temperature for 30 min to generate a uniform aqueous solution. The use of a high excess of NaBH$_4$ ensures that its concentration remains essentially constant during the whole reaction, which allows the assumption of pseudo-first-order kinetics with respect to the nitro compound. Samples of the reaction mixture were collected at specific time intervals for UV-vis spectroscopy analysis.

Results

As shown in the, UV-vis absorption spectra of 4-nitrophenol in FIG. 5(a-c) and 16, a peak at 400 nm corresponding to 4-NP gradually attenuates with a peak at 300 nm attributable to 4-AP increasing concomitantly, which suggests successful reduction of 4-NP to 4-AP. It has been well-established that catalytic selective reduction of 4-NP to 4-AP follows a pseudo-first-order kinetic reaction. As displayed in FIGS. 5(c-e), catalytic performances of all multilayer films are closely related to assembly layer, among which (Au/GQDs)$_{10}$ film demonstrated the highest rate constant (0.345 min-) in comparison with (Au)$_{10}$ (0.091 min-) and (GQDs)$_{10}$ (0.030 min-) counterpart films with the same assembly layer, suggesting that synergistic effect (FIG. 5g) between Au NCs and GQDs contributes to the significantly enhanced catalytic performances of composite films. Analogous results were observed in the catalytic performance of (Au/GR)$_n$ (n=1, 5, 10, 15) multilayer hybrid films (FIG. 17) which also exhibited much higher catalytic activities than (Au)$_n$ and (GQDs)$_n$ films with the same assembly layer. The results indicated that synergistic interaction between Au NCs and GR in (Au/GR)$_n$ films are also responsible for the enhancement of catalytic activities and this may be predominantly ascribed to the intimate interfacial interaction between metal (Au) and carbon materials (GQDs and GR) afforded by LbL assembly. It is worth noting that (Au/GQDs)$_n$ films exhibited remarkably improved catalytic activities relative to (Au/GR)$_n$ films. The rate constant of (Au/GQDs)$_{10}$ film is almost three times higher than that of (Au/GR)$_n$ under the same conditions i.e., (0.345 vs. 0.126 min-), implying GQDs is much more active than GR in boosting the selective reduction performances of multilayer composite films. This observation can be attributed to the different dimensionality between GQDs and GR, which affords varied number of active sites. 0D GQDs possesses a greater number of active sites on the planar surface compared with 2D GR due to its ultra-small size, thereby facilitating adsorption and reaction of reactants. Moreover, it was found that (Au/GQDs)$_{10}$ film demonstrated favorable catalytic stability which is reflected in the catalysts recycling experiments. Specifically, as shown in FIG. 5h, no attenuation of catalytic performance was seen over (Au/GQDs)$_{10}$ film even after four successive recycles, this confirms that the (Au/GQDs)$_{10}$ film is stable during the catalytic process. To confirm that the (Au/GQDs)$_{10}$ film remained stable during the catalytic reaction, an AFM image of the (Au/GQDs)$_{10}$ film was obtained before and after a cycle of catalytic reaction. The image (FIG. 23) revealed an unaltered, uniform structure.

The promising catalytic performances were also observed over other (M/GQDs)$_{10}$ (M=Ag, Pt) multilayer films and, among which, (Au/GQDs)$_{10}$ demonstrated the most efficient catalytic activity. The predominant reason accounting for the remarkably enhanced catalytic activities of (Au/GQDs)$_n$ films is proposed to be the dual functionality of GQDs layer facilitating the adsorption of 4-NP molecules owing to analogous structure and thus boosting the reaction kinetics, and also preventing the agglomeration of metal NCs hence enhancing the stability of multilayer composite film. The highly efficient catalytic activities and stability of the (M/GQDs)$_{10}$ multilayer composite films (FIG. 5i & FIG. 18) are of great significance in practical applications, especially in aqueous media, because no separation of catalyst is needed by virtue of the direct formation of multilayer films on the substrate.

To demonstrate the versatile catalytic properties of these LbL assembled multilayer films, selective catalytic reduction of other aromatic nitro compounds including 2-NP, 3-NP, 4-NA, 2-NA, and 3-NA to corresponding amino compounds were further explored. As shown in FIG. 6, consistently, (M/GQDs)$_{10}$ (M=Au, Ag, Pt) multilayer films demonstrated markedly enhanced catalytic activities toward the reduction of a series of aromatic nitro compounds at ambient conditions in comparison with $(Au)_{10}$ and $(GQDs)_{10}$ counterpart multilayer thin films under the same conditions and catalytic performances of different samples followed the same order of: $(M/GQDs)_{10}>(M)_{10}>(GQDs)_{10}$. Additionally, it was found that $(Au/GQDs)_{10}$ film always demonstrated the most enhanced catalytic performances among $(M/GQDs)_{10}$ (M=Au, Ag, Pt) films implying metal-dependent catalytic activities of multilayer films. The corresponding reaction rate constants of $(Au)_{10}$, $(GQDs)_{10}$, and $(Au/GQDs)$ multilayer thin films were summarized in Table 1.

TABLE 1

Catalytic reaction rate constants of different sample toward reduction of aromatic nitro compounds with an excess amount of $NaBH_4$ in aqueous media at ambient temperature. Unit: $min^{-1}$

| Sample | 4-NA | 3-NA | 2-NA | 4-NP | 3-NP | 2-NP |
|---|---|---|---|---|---|---|
| $Au_{10}$ | 0.091 | 0.103 | 0.097 | 0.102 | 0.118 | 0.109 |
| $GQDs_{10}$ | 0.030 | 0.038 | 0.034 | 0.041 | 0.051 | 0.043 |
| $(Au/GQDs)_{10}$ | 0.345 | 0.406 | 0.354 | 0.398 | 0.417 | 0.403 |
| $(Ag/GQDs)_{10}$ | 0.201 | 0.346 | 0.312 | 0.304 | 0.386 | 0.355 |
| $(Pt/GQDs)_{10}$ | 0.289 | 0.353 | 0.337 | 0.307 | 0.369 | 0.363 |

Example 3: Electrochemical Methanol Oxidation

The synthesized assembled $(Au/GQDs)_n$ (n=1, 5, 10, 15) hybrid thin films toward methanol oxidation were first measured under the cyclic voltammetry experiment in a 0.10 M KOH solution with and without $CH_3OH$ in $N_2$ atmosphere (FIG. 7).

Method

Electrochemical experiments were carried out in a three-electrode quartz cell with electrochemical workstation (CHI 66D) in which platinum sheet was employed as counter electrode and Ag/AgCl electrode as reference electrode, and the $(M/GQDs)_n$ samples with an active area of 15.9 $mm^2$, provided by a mask with a diameter of 4.5 mm, were used as the working electrodes. Cyclic voltammetry (CV) and linear sweep voltammetry (LSV) were performed between 0.00 to 0.75 V in 0.1 M KOH solution with or without 1.0 M methanol solution at room temperature at a scan rate of 20 mV/s. Electrochemical impedance spectroscopy (EIS) measurements were performed in the frequency range from 100 kHz to 100 mHz under AC stimulus of 10 mV in amplitude.

Results

Without $CH_3OH$, the curve during the forward sweep performance exhibits an obvious onset potential of 0.45 V (vs SCE), which is ascribed to the progress of adopting $OH^-$ and subsequently oxidation on Au NCs surface as represented in the following reaction (1) and (2).

$$Au+OH^- \rightarrow Au\text{---}OH^{(1-\lambda)-}+\lambda e^- \quad (1)$$

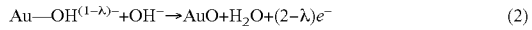
$$Au\text{---}OH^{(1-\lambda)-}+OH^- \rightarrow AuO+H_2O+(2-\lambda)e^- \quad (2)$$

where $\lambda$ means the charge transfer coefficient, and it varies between 0 (for a non-faradaic reaction) and 1 (for a faradaic reaction).

The backward sweep performance shows a reduction peak at 0.3 V, corresponding to the reduction of metal oxide and desorption of $OH^-$ from Au NCs. It should be emphasized that both oxidation and reduction peaks can be observed nearly at the same position irrespective of the number of layer during forward and backward sweep performances; however, the sample $(Au/GQDs)_{10}$ generally exhibited superior electrocatalytic activity to other multilayer thin films. In addition, the current density of the $(Au/GQDs)_n$ multilayer films becomes large with increasing the number of layers (n), up to 10; nevertheless, the current density subsequently decreased when n increase to more than 10. When methanol (1.0 M) was being added to the solution, dramatic changing of the cyclic voltammograms appeared; for instance, oxidation peaks at 0.52 V and reduction peak at 0.35 V become large for the $(Au/GQDs)_{10}$ thin film. Analogous to the selective chemical catalytic performance, $(Au/GQDs)_{10}$ thin film shows better electrocatalytic activity relative to individual Au NCs or GQDs alone due to the synergistic catalytic effects of each component (FIG. 7c). More stringent measurements on stability are necessary for fuel cell studies, nevertheless, it can be observed that the electrochemical response of $(Au/GQDs)_{10}$ hybrid thin film reserve stability over 100 cycles with a retention of 89% (FIG. 7e). As a clear comparison, the Au NCs without GQDs exhibit a pronounced cyclic instability of 41% and a smaller current density (0.013 $mA/cm^2$ vs 0.174 $mA/cm^2$ of $(Au/GQDs)_{10}$ thin film) (FIG. 7d), suggesting the critical role of GQDs as a chemically stable component in inhibiting inactivation of catalytic site in Au NCs during cyclic voltammograms experiment. Moreover, $(Ag/GQDs)_{10}$ and $(Pt/GQDs)_{10}$ hybrid thin film also show comparable high-efficiency electrocatalytic performance (FIG. 7f).

$(Au/GQDs)_{10}$ thin films samples were further investigated in the electrochemical measurements of methanol oxidation. By cyclic voltammetry test of $(Au/GQDs)_{10}$ thin films samples, it can be found that the square root of scan rates are linearly proportional to the anodic peak currents, exhibiting the electrocatalytic activity of methanol oxidation is mainly diffusion-controlled (FIG. 8a,b). When increasing the methanol concentration, the anodic current peaks are linearly increased with methanol concentration as displayed in FIG. 8c. The cathodic peak currents, however, become lower under the increasing concentration of methanol, indicative of reducing surface oxidation when negative potential is applied. It should be noted that the cathodic peak current tend to disappear when the methanol concentration is larger than 3.0 M which might be due to the Au oxide coverage being too thick. Analogous results were also observed in the methanol oxidation over $(Au/GR)_{10}$ multilayer thin films (FIG. 24), again verifying the general applicability and versatility of the current LbL assembly strategy. Tafel plots of $(Au/GQDs)_{10}$ multilayer thin films for methanol oxidation using different methanol concentration at a scan rate of 50 mV/s were shown in FIG. 8e. clearly indicating a linear correlation for log/vs. potential was in the Tafel range. Tafel slope for $(Au/GQDs)_{10}$ film was determined to be 251.6 mV/dec in the potential range of 0.3-0.4 V (vs. Ag/AgCl) and the transfer coefficient was calculated to be 0.18, indicating the first charge transfer process is rate-determining step. The overall reaction order of methanol oxidation at fixed potentials can be obtained from the slope of the straight line fit (0.61) (FIG. 25). This result suggested that the kinetic parameters of methanol oxidation over $(Au/GQDs)_{10}$ multilayer film remain unchanged in the Tafel range with increasing the methanol concentration.

The kinetics and interfacial resistance of samples can be further provided by using electrochemical impedance spectroscopy to evaluate the electrochemical progress (Lee, E. P. et al., Acs Nano 2008, 2, 2167-2173; Chang, B. Y. et al., Annu Rev Anal Chem 2010, 3, 207-229). The interfacial charge-transfer resistances at the $(Au/GQDs)_n$ electrode during methanol oxidation reaction are measured with the variation of layer numbers. As evaluated in FIG. 8e,f, the Nyquist plot verified the interfacial charge-transfer resistances values of $(Au/GQDs)_{10}$ thin film that are lower than those of other thin films, such as 209390 ohm $((Au/GQDs)_{01})$, 80041 ohm $((Au/GQDs)_{01})$, 1950 ohm $((Au/GQDs)_{10})$, 12083 ohm $((Au/GQDs)_{15})$, 3063 ohm $((Ag/GQDs)_{10})$, 13393 ohm $((Pt/GQDs)_{10})$, respectively. Meanwhile, the Nyquist plot suggests that the 10-layer $(M/GQDs)_{10}$ thin films possesses lower interfacial resistance which could provide an enhanced catalytic performance toward methanol oxidation. This result indicates $(Au/GQDs)_{10}$ thin films exhibit the better electrocatalytic activities than that of the other thin films which is in good agreement with the previous catalytic performance, highlighting the practical potential of LbL self-assembly in fine tuning the catalytic performance of the current system toward the development of more efficient catalysts and/or electrocatalysts.

Example 4: Photoelectrochemical Water Splitting

Photoelectrochemical (PEC) performances of $(M/GQDs)_n$ multilayer thin films were probed to unveil the fate of light-induced electron-hole charge carriers on the interfacial region of metal NCs and GQDs.

Photoelectrochemical (PEC) Measurement

PEC measurements were carried out on an electrochemical workstation (Zennium, Zahner). The electrochemical setup is composed of conventional three-electrodes, a quartz cell containing 20 mL $Na_2SO_4$ (0.5 M) aqueous solution and a potentiostat. A platinum plate (20 mm×10 mm) was used as counter electrode and Ag/AgCl as reference electrode. The sample films (20 mm×10 mm) were vertically dipped into electrolyte and irradiated with a 300 W xenon arc lamp (Newport) equipped with an AM 1.5 filter. Monochromatic incident photo-to-electron conversion efficiency (IPCE) spectra were collected using three-electrode without bias, for which monochromatic light was provided by a 300 W xenon arc lamp (Newport) combined with a monochromator (Newport).

As displayed in FIG. 21a, photocurrent of $(Au/GQDs)_{10}$ is substantially higher than that of $(Au)_{10}$ and $(GQDs)_{10}$ under the same conditions. $(Au)_{10}$ demonstrated nearly no detectable photocurrent, but the photocurrent of $(Au/GQDs)_{10}$ is almost three-fold higher than $(GQDs)_{10}$. The results indicate that photogenerated electron-hole pairs were produced over GQDs which can serve as a semiconductor for bandgap photoexcitation. The result suggests that alternate integration of Au NCs with GQDs in a unique stacked fashion via LbL assembly is beneficial for producing significantly enhanced photocurrent of $(Au/GQDs)_n$ multilayer film.

The analogous results were also observed in the LSV results of different multilayer films, thus confirming the cooperative synergy of Au and GQDs for photocurrent generation and enhancement (FIG. 21b). The significantly improved photocurrent of $(Au/GQDs)_n$ in comparison with $(Au)_n$ and $(GQDs)_n$ films indicates a more effective separation of photogenerated electrons and holes over $(Au/GQDs)_n$, in which Au NCs may play dual roles including SPR photosensitizer for producing hot electrons or electron traps for capturing photogenerated electrons from GQDs. Consistently, EIS Nyquist plots of $(Au/GQDs)_{10}$ (FIG. 21c) exhibited the smallest semicircle arc radius relative to $(Au)_{10}$ and $(GQDs)_{10}$, further verifying the most efficient interfacial electron transfer rate was imparted by the synergistic interaction of Au NCs and GQDs. FIG. 21d shows the on-off transient photocurrent responses of $(Au/GQDs)_n$ multilayer thin films under chopped simulated solar light illumination. Significantly, all $(Au/GQDs)_n$ multilayer thin films demonstrated transient photocurrent responses which increases with boosting the assembly cycle and thus, the result reflects tunable PEC performances of $(Au/GQDs)_n$ film. Moreover, it was found that interfacial charge transfer efficiency is closely related to the assembly cycle and this can be reflected by the EIS results of $(Au/GQDs)_n$ film with varying assembly cycle (FIG. 21f). As displayed in FIG. 26, 80% photocurrent of $(Au/GQDs)_{10}$ was retained under continuous simulated solar light irradiation, indicative of favorable photostability of $(Au/GQDs)_{10}$ film. Apart from $(Au/GQDs)_n$, $(Ag/GQDs)_n$ and $(Pt/GQDS)_n$ multilayer thin films also demonstrated transient photocurrent responses under simulated solar light irradiation and it follows the order of: $(Au/GQDs)_{10} > (Ag/GQDs)_{10} > (Pt/GQDs)_{10} > (GQDs)_{10}$, among which $(Au/GQDs)_{10}$ film exhibited the most enhanced photocurrent (FIGS. 21g and h) and the smallest charge transfer resistance (FIG. 21i). Therefore, it can be concluded that PEC performances of $(M/GQDs)_n$ multilayer thin films can not only be tuned by assembly cycle, but also the type of metal NCs. Incident photo-to-current conversion efficiency (IPCE) measurements were performed to determine the active wavelength region contributing to the generation of photocurrent. As displayed in FIG. 27, IPCE results of $(Au/GQDs)_n$ multilayer films exhibited two peaks at ca. 355 and 530 nm which were attributable to the characteristic peaks of GQDs and Au NCs, respectively. These results show the synergistic roles of Au NCs and GQDs in producing photocurrent under simulated solar light irradiation.

The invention claimed is:

1. A multilayered composite thin film material comprising:
    a substrate having a positively-charged surface;
    a first bilayer material comprising:
        a layer of metal nanocrystal particles, each particle having a negatively charged surface, wherein the metal is selected from the group consisting of Ru, Rh, Os, Ir, Pd, Au, Ag and Pt, and the particles are attached to the substrate surface by charge attraction; and
        a coating layer of graphene quantum dots, each graphene quantum dot having a positively charged surface and attached to the layer of metal nanocrystal particles by charge attraction; and
    a 0 to $n^{th}$ additional bilayers comprising:
        a layer of metal nanocrystal particles, each particle having a negatively charged surface, wherein the metal is selected from the group consisting of Ru, Rh, Os, Ir, Pd, Au, Ag and Pt, and the particles are attached to the preceding layer of graphene quantum dots by charge attraction; and
        a coating layer of graphene quantum dots, each graphene quantum dot having a positively charged surface and attached to the layer of metal nanocrystal particles by charge attraction, wherein
        n is from 1 to 49, and
        the graphene quantum dots have a particle size of from 3 to 20 nm.

2. The composite material according to claim 1, wherein n is from 1 to 19.

3. The composite material according to claim 1, wherein the positively charged surface of the graphene quantum dots is provided by covalently bonded moieties comprising an ammonium ion functional group.

4. The composite material according to claim 1, wherein the graphene quantum dots have one or more properties selected from:
(a) a thickness of from about 0.7 to about 1.2 nm, or a thickness of from 1 to 2 layers of graphene; and
(b)) a measured zeta potential of from +40 mV to +70 mV when measured using a pH profile of from pH 7 to 12.

5. The composite material according to claim 1, wherein the negatively charged surface of the metal nanocrystals is provided by moieties comprising carboxylate ions.

6. The composite material according to claim 1, wherein the metal nanocrystals have one or more of:
(a) an average diameter of from 3 nm to 20 nm;
(b) a measured zeta potential of from −30 mV to −60 mV when measured using a pH profile of from pH 6 to 12; and
(c) each layer of metal nanocrystal particles comprise a metal selected from the group consisting of Pd, Au, Ag and Pt.

7. The composite material according to claim 1, wherein the composite has an image-average current of from 20 to 500 pA as measured by conductive atomic force microscopy.

8. The composite material according to claim 1, wherein the metal nanocrystals are citrate-stabilized metal nanocrystals.

9. The composite material according to claim 1, wherein the metal nanocrystals are one or more of:
(a) gold nanocrystals having an average particle size of from 12 to 17 nm;
(b) silver nanocrystals having an average particle size of from 5 to 8 nm; and
(c) platinum nanocrystals having an average particle size of from 2 to 4 nm.

10. The composite material according to claim 1, wherein the metal nanocrystals are citrate-stabilized gold nanocrystals, n is 9 and the composite material has an image-average current of from 150 to 200 pA as measured by conductive atomic force microscopy.

11. The composite material according to claim 1, wherein the substrate is selected from one or more of the group consisting of fluorine-doped tin oxide, glass, silicon, indium tin oxide (ITO), and titanium.

12. The composite material according to claim 1, wherein the positively charged surface of the substrate is provided by a polycationic polymer selected from the group consisting of polyethylenimine, poly(diallyldimethylammonium chloride) (PDDA), copolymers thereof, and blends thereof.

13. A method of assembling the multilayered composite thin film material according to claim 1, comprising the steps of:
(a) providing a substrate having a positively charged surface;
(b) dipping the substrate into a first solution comprising negatively charged metal nanocrystals, subsequently washing and drying the dipped material to form a negatively charged surface of metal nanocrystals;
(c) dipping the product of step (b) into a second solution comprising positively charged graphene oxide quantum dots, subsequently washing and drying the dipped material to form a positively charged surface;
(d) optionally repeating steps (b) and (c) n times using the product of step (c) as the substrate;
(e) subjecting the product of step (c) or, when conducted, step (d) to an annealing step under heat and an inert atmosphere, wherein:
n is from 1 to 49; and
the metal nanocrystals used in each step (b) are independently selected from the group consisting of Ru, Rh, Os, Ir, Pd, Au, Ag and Pt.

14. A method of catalyzing an organic reaction comprising contacting one or more reagents for the organic reaction with the composite material according to claim 1 and providing the conditions necessary to effect the organic reaction.

15. The method of claim 14, wherein the organic reaction is the catalytic reduction of aromatic nitro compounds to aromatic amine compounds in the presence of a reducing agent.

16. The method of claim 14, wherein the organic reaction is the oxidation of methanol in an electrocatalytic reaction to produce carbon dioxide.

17. A device useful for photodetection and/or energy harvesting comprising a composite material according to claim 1.

18. The device according to claim 17, wherein the composite material is provided as part of an electrode.

19. A method of energy harvesting involving the steps of:
(a) providing a light-transparent device comprising a working electrode that comprises a composite material according to claim 1, at least one other electrode as a counter electrode and an electrolyte;
(b) irradiating the device with light to generate a photocurrent; and
(c) converting water to hydrogen and oxygen.

* * * * *